(12) United States Patent
Ebert et al.

(10) Patent No.: US 7,524,634 B2
(45) Date of Patent: Apr. 28, 2009

(54) MN/CA IX AND CANCER PROGNOSIS

(75) Inventors: Matthias Ebert, München (DE); Christoph Röcken, Magdeburg (DE); Silvia Pastorekova, Stupava (SK); Jan Zavada, Prague (CZ); Jaromir Pastorek, Stupava (SK)

(73) Assignee: Institute of Virology, Slovak Academy of Sciences, Bratislava (SK)

( * ) Notice: Subject to any disclaimer, the term of this patent is extended or adjusted under 35 U.S.C. 154(b) by 0 days.

(21) Appl. No.: 10/575,300

(22) PCT Filed: Oct. 18, 2004

(86) PCT No.: PCT/US2004/034573

§ 371 (c)(1),
(2), (4) Date: Sep. 18, 2006

(87) PCT Pub. No.: WO2005/037083

PCT Pub. Date: Apr. 28, 2005

(65) Prior Publication Data

US 2007/0042376 A1 Feb. 22, 2007

(51) Int. Cl.
*G01N 33/53* (2006.01)
(52) U.S. Cl. ...................................... 435/7.1
(58) Field of Classification Search ................ 435/7.1
See application file for complete search history.

(56) References Cited

U.S. PATENT DOCUMENTS

| 5,387,676 A | 2/1995 | Zavada et al. | 536/23.5 |
| 5,989,838 A | 11/1999 | Zavada et al. | 435/7.23 |
| 6,004,535 A | 12/1999 | Zavada et al. | 424/9.34 |

OTHER PUBLICATIONS

Bui et al (Clinical Cancer Research, Feb. 2003, 9:802-811).*
Tockman et al (Cancer Res., 1992, 52:2711s-2718s).*
Pastorekov and Zavada (Cancer Therapy, 2004, 2:245-262).*
Tatum et al (Int J Radiat Biol, 2006, 82(10):699-757).*
Potter and Harris (Cell Cycle, 2004, 3(2): 164-167).*
Matsumura et al (Neurol Med Chir, 1997, 37:abstract).*
Hicks et al (Urol Int, 2003, 70(3):abstract).*
Young et al (Int J Gynecol Pathol, 1992, 11(2):abstract).*
Ishizawa et al (Asian Journal of Surgery, Jul. 2006, 29(3):145-148).*
Ivanov et al (American Journal of Pathology, 158(3): 905-19).*
Ashida et al., "Effects of von Hippel-Lindau gene mutation and methylation status on expression of transmembrane carbonic anhydrases in renal cell carcinoma," *J Cancer Res Clin Oncol*,128: 561-568 (2002).
Brewer et al., "A Study of Biomarkers in Cervical Carcinoma and Clinical Correlation of the Novel Biomarker MN," *Gynecologic Oncology* 63: 337-344 (1996).
Bui et al., "Carbonic Anhydrase IX Is an Independent Predictor of Survival in Advanced Renal Clear Cell Carcinoma: Implications for Prognosis and Therapy," *Clin. Cancer Res.*, 9: 802-811 (2003).

Chen et al., "Expression of CA9 at the invasion front of gastric cancers," *Gut*, 54(7): 920-927 (2005).
Chia et al., "Prognostic significance of a novel hypoxia-regulated marker, carbonic anhydrase IX, in invasive breast carcinoma," *J Clin Oncol*, 19: 3660-3668 (2001).
Cho et al., "Hypomethylation of the MN/CA9 promoter and upregulated MN/CA9 expression in human renal cell carcinoma," *Br J Cancer*, 85: 563-567 (2001).
Chrastina et al., "Biodistribution and pharmacokinetics of 125I-labeled monoclonal antibody M75 specific for carbonic anhydrase IX, an intrinsic marker of hypoxia, in nude mice xenografted with human colorectal carcinoma." *Int J Cancer*, 105(6): 873-881 (2003).
Giatromanolaki et al. "Expression of hypoxia-inducible carbonic anhydrase-9 relates to angiogenic pathways and independently to poor outcome in non-small cell lung cancer," *Cancer Res*, 61:7992-7998 (2001).
Ivanov et al., "Expression of hypoxia-inducible cell-surface transmembrane carbonic anhydrases in human cancer." *Am J Path*, 158(3): 905-919 (2001).
Juhasz et al., "Expression of carbonic anhydrase IX in human pancreatic cancer," *Aliment Pharmacol Ther*, 18: 837-846 (2003).
Karhumaa et al., "Expression of the transmembrane carbonic anhydrases, CA IX and CA XII, in the human male excurrent ducts," *Mol Hum Reprod*, 7: 611-616 (2001).
Kivela et al., "Differential expression of cytoplasmic carbonic anhydrases, CA I and II, and membrane-associated isozymes, CA IX and XII, in normal mucosa of large intestine and in colorectal tumors." *Dig Dis Sci*, 46(10): 2179-2186 (2001).
Kivela et al., "Expression of transmembrane carbonic anhydrase isozymes IX and XII in normal human pancreas and pancreatic tumours," *Histochem Cell Biol*, 114: 197-204 (2000).
Koukourakis et al., "Hypoxia-regulated carbonic anhydrase-9 (CA9) relates to poor vascularization and resistance of squamous cell head and neck cancer to chemoradiotherapy," *Clin Cancer Res*, 7: 3399-3403 (2001).

(Continued)

*Primary Examiner*—Sean E Aeder
(74) *Attorney, Agent, or Firm*—Lieona L. Lauder; Joan C. Harland; Barbara A. Shimei

(57) ABSTRACT

Herein disclosed are methods that are prognostic for neoplastic/preneoplastic disease in a subject vertebrate, wherein said disease is associated with a tissue that normally expresses MN, but which MN expression is lost or diminished upon carcinogenesis. Exemplary of the types of preneoplastic/neoplastic diseases subject to the prognostic methods of this invention are those of gastric mucosa, gallbladder, biliary ducts, and ductal cells of duodenal glands. An exemplary prognostic method comprises comparing the level of MN gene expression product in a tissue sample from the affected subject, with the average MN gene expression product level found in analogous preneoplastic/neoplastic tissue samples; an above average MN gene expression product level indicates poorer prognosis for the subject. MN gene expression products useful in the prognostic methods include MN protein, MN polypeptide, and/or MN nucleic acids.

15 Claims, 14 Drawing Sheets

OTHER PUBLICATIONS

Leppilampi et al., "Carbonic anhydrase isozymes IX and XII in gastric tumors," *World J Gastroenterol*, 9: 1398-1403 (2003).

Liao et al. "Identification of the MN antigen as a diagnostic biomarker of cervical intraepithelial neoplasia and cervical carcinoma," *Am J Pathol*,145: 598-609 (1994).

Loncaster et al., "Carbonic anhydrase expression, a potential new intrinsic marker of hypoxia: correlations with tumor oxygen measurements and prognosis in locally advanced carcinoma of the cervix," *Cancer Res*, 61: 6394-6399 (2001).

Moss et al., "Inward growth of colonic adenomatous polyps," *Gastroenterology*, 111: 1425-1432 (1996).

Nishimori et al., "Carbonic anhydrase in human pancreas: hypotheses for the pathophysiological roles of CA isozymes." *Ann N Y Acad Sci.*, 880: 5-16 (1999).

Ortova Gut et al., "Gastric hyperplasia in mice with targeted disruption of the carbonic anhydrase gene Car9," *Gastroenterology*, 123: 1889-1903 (2002).

Parkkila and Parkkila, "Carbonic anhydrase in the alimentary tract. Roles of the different isozymes and salivary factors in the maintenance of optimal conditions in the gastrointestinal canal," *Scand J Gastroenterol.*, 31: 305-317 (1996).

Parkkila et al., "Carbonic anhydrase inhibitor suppresses invasion of renal cancer cells in vitro," *Proc Natl Acad Sci (USA)*, 97: 2220-2224 (2000).

Pastorek et al., "Cloning and characterization of MN, a human tumor-associated protein with a domain homologous to carbonc anhydrase and a putative helix-loop-helix DNA binding segment," *Oncogene*, 9: 2877-2888 (1994).

Pastorekova and Zavada, "Carbonic anhydrase IX (CA IX) as a potential target for cancer therapy," *Cancer Therapy*, 2: 245-262 (2004).

Pastorekova et al., "A Novel Quasi-viral Agent, MaTu, Is a Two-Component System," *Virology*, 187: 620-626 (1992).

Pastorekova et al., "Carbonic Anhydrase IX: Analysis of stomach complementary DNA sequence and expression in human and rat alimentary tracts," *Gastroenterology*, 112: 398-408 (1997).

Potter and Harris, "Diagnostic, prognostic and therapeutic implications of carbonic anhydrases in cancer," *Br J Cancer*, 89: 2-7 (2003).

Risio, M., "Cell proliferation in colorectal tumor progression: an immunohistochemical approach to intermediate biomarkers," *J. Cell Biochem*, 16G: 79-87 (1992).

Saarnio et al., "Immunohistochemical study of colorectal tumors for expression of a novel transmembrane carbonic anhydrase, MN/CA IX, with potential value as a marker of cell proliferation," *Am J Pathol*, 153: 279-285 (1998).

Saarnio et al., "Transmembrane carbonic anhydrase, MN/CA IX, is a potential biomarker for biliary tumors," *J Hepatol*, 35: 643-649 (2001).

Swinson et al., "Carbonic anhydrase IX expression, a novel surrogate marker of tumor hypoxia is associated with a poor prognosis in non-small cell lung cancer," *J Clin Oncol*, 21: 473-482 (2003).

Turner et al., "MN antigen expression in normal, preneoplastic, and neoplastic esophagus: A clinicopathological study of a new cancer-associated biomarker," *Human Pathol*, 28: 740-744 (1997).

Uemura et al., "MN/CA IX/G250 as a potential target for immunotherapy of renal call carcinomas," *Br. J. Cancer*, 81:741-746 (1999).

Wykoff et al. "Hypoxia-inducible expression of tumor-associated carbonic anhydrases," *Cancer Res*, 60: 7075-7083 (2000).

Zavada et al., "Expression of MaTu-MN protein in human tumor cultures and in clinical specimens," *Int J Cancer*, 54: 268-274 (1993).

Zhong et al., "Overexpression of hypoxia-inducible factor lalpha in common human cancers and their metastases," *Cancer Res*, 59: 5830-5835 (1999).

Tatum et al., "Hypoxia: Importance in tumor biology, noninvasive measurement by imaging, and value of its measurement in the management of cancer therapy," *Int. J. Radiat. Biol.*, 82(10): 669-757 (Oct. 2006).

Ashida et al., "Effects of von Hippel-Lindau gene mutation and methylation status on expression of transmembrane carbonic anhydrases in renal cell carcinoma," *J. Cancer Res. Clin. Oncol.*, 128: 561-568 (2002).

Driessen et al., "Expression of Carbonic Anhydrase IX (CA IX), a Hypoxia-Related Protein, Rather Than Vascular-Endothelial Growth Factor (VEGF), a Pro-Angiogenic Factor, Correlates With an Extremely Poor Prognosis in Esophageal and Gasric Adenocarcinomas," *Annals of Surgery*, 243(3): 334-340 (Mar. 2006).

Ivanov et al., "Expression of Hypoxia-Inducible Cell-Surface Transmembrane Carbonic Anhydrases in Human Cancer," *American Journal of Pathology*, 158(3): 905-919 (Mar. 2001).

Robertson et al., "Role of Carbonic Anhydrase IX in Human Tumor Cell Growth, Survival, and Invasion," *Cancer Research*, 64: 6160-6165 (Sep. 1, 2004).

Saarnio et al., "Transmembrane carbonic anhydrase, MN/CA IX, is a potential biomarker for biliary tumours," *Journal of Hepatology*, 35: 643-649 (2001).

Svastova et al., "Hypoxia activates the capacity of tumor-associated carbonic anhydrase IX to acidify extracellular pH," *FEBS Letters*, 577: 439-445 (2004).

\* cited by examiner

FIG._1A

| | | | | | | | | | | | | | |
|---|---|---|---|---|---|---|---|---|---|---|---|---|---|
| 1 | | | | M | A | P | L | C | P | S | P | W | L | L | 12 |
| 1 | ACA | GTC | AGC | CGC | ATG | GCT | CCC | CTG | TGC | CCC | AGC | TGG | CTC | CTG | 48 |
| 13 | L | I | P | A | P | A | P | G | L | T | V | Q | L | S | 28 |
| 49 | TTG | ATC | CCG | GCC | CCT | GCT | CCA | GGC | CTC | ACT | GTG | CAA | CTG | TCA | 96 |
| 29 | L | L | L | M | P | V | H | P | Q | R | L | P | M | Q | 44 |
| 97 | CTG | CTT | CTG | ATG | CCT | GTC | CAT | CCC | CAG | AGG | TTG | CCC | ATG | CAG | 144 |
| 45 | E | D | S | P | L | G | G | G | S | S | G | E | D | L | 60 |
| 145 | GAG | GAT | TCC | CCC | TTG | GGA | GGC | TCT | TCT | GGG | GAA | GAG | CCA | CTG | 192 |
| 61 | G | E | E | D | L | P | S | E | E | D | S | P | R | E | D | 76 |
| 193 | GGC | GAG | GAG | GAT | CTG | CCC | AGT | GAG | GAG | GAT | TCA | CCC | AGA | GAG | GAT | 240 |
| 77 | P | P | G | E | E | L | D | E | E | G | P | L | E | E | 92 |
| 241 | CCA | CCC | GGA | GAG | GAG | CTA | GAT | GAG | GAG | GGA | CCT | CTA | GAG | GAG | 288 |
| 93 | E | D | L | P | E | V | K | P | K | S | E | E | E | L | 108 |
| 289 | GAG | GAT | CTA | CCT | GAA | GTT | AAG | CCT | AAA | TCA | GAA | GAA | GAG | CTG | 336 |
| 109 | K | L | E | D | L | P | T | V | E | A | P | G | D | E | 124 |
| 337 | AAG | TTA | GAG | GAT | CTA | CCT | ACT | GTT | GAG | GCT | CCT | GGA | GAT | GAA | 384 |
| 125 | P | Q | N | A | H | R | D | K | E | G | D | D | Q | S | H | 140 |
| 385 | CCC | CAG | AAT | AAT | GCC | CAC | AGG | GAC | AAA | GAA | GGG | GAT | GAC | CAG | AGT | CAT | 432 |
| 141 | W | R | Y | G | D | P | P | W | P | R | V | S | P | A | C | 156 |
| 433 | TGG | CGC | TAT | GGA | GAC | CCG | CCC | TGG | CCC | CGG | GTG | TCC | CCA | GCC | TGC | 480 |
| 157 | A | G | F | Q | R | V | P | S | D | I | R | P | Q | L | A | 172 |
| 481 | GCG | GGC | TTC | CAG | CGC | GTG | CCG | TCC | GAT | ATC | CGC | CCC | CAG | CTC | GCC | 528 |

| | | | | | | | | | | | |
|---|---|---|---|---|---|---|---|---|---|---|---|
| 173 | F | C | P | A | L | R | P | L | E | L | L | G | F | Q | L | P | 188 |
| 529 | TTC | TGC | CCG | GCC | CTG | CGC | CCC | CTG | GAA | CTC | CTG | GGC | TTC | CAG | CTC | CCG | 576 |
| 189 | P | L | P | E | L | R | L | R | N | N | G | H | S | V | Q | L | 204 |
| 577 | CCG | CTC | CCA | GAA | CTG | CGC | CTG | CGC | AAC | AAT | GGC | CAC | AGT | GTG | CAA | CTG | 624 |
| 205 | T | L | P | L | G | L | E | M | A | L | G | P | G | R | E | Y | 220 |
| 625 | ACC | CTG | CCT | GGG | CTA | CTG | GAG | ATG | GCT | CTG | GGT | CCC | GGG | CGG | GAG | TAC | 672 |
| 221 | R | A | L | Q | H | L | H | L | W | G | A | A | G | R | P | G | 236 |
| 673 | CGG | GCT | CTG | CAG | CAT | CTG | CAC | CTG | TGG | GGG | GCA | GCT | GGT | CGT | CCG | GGC | 720 |
| 237 | S | E | H | T | V | E | G | H | R | F | P | A | E | I | H | V | 252 |
| 721 | TCG | GAG | CAC | ACT | GTG | GAA | GGC | CAC | CGT | TTC | CCT | GCC | GAG | ATC | CAC | GTG | 768 |
| 253 | V | H | L | S | T | A | F | A | R | V | D | E | A | L | G | R | 268 |
| 769 | GTT | CAC | CTC | AGC | ACC | GCC | TTT | GCC | AGA | GTT | GAC | GAG | GCC | TTG | GGG | CGC | 816 |
| 269 | P | G | G | L | A | V | L | A | F | L | E | E | G | E | P | E | 284 |
| 817 | CCG | GGA | GGC | CTG | GCC | GTG | TTG | GCC | TTT | CTG | GAG | GAG | GGC | GAG | CCG | GAA | 864 |
| 285 | E | N | S | A | Y | E | Q | S | L | R | L | D | I | S | A | I | 300 |
| 865 | GAA | AAC | AGT | GCC | TAT | GAG | CAG | TCT | CGC | CTG | GAC | ATA | TCT | GCA | ATC | GCT | 912 |
| 301 | E | G | S | E | T | Q | R | G | L | Y | E | G | S | L | T | L | 316 |
| 913 | GAG | GGC | TCA | GAG | ACT | CAG | CGC | GGA | CTG | TAT | GAG | GGG | TCT | CTG | ACT | CTC | 960 |
| 317 | L | P | S | D | F | S | Q | Y | F | Q | W | F | V | T | L | T | 332 |
| 961 | CTG | CCC | TCT | GAC | TTC | AGC | CAA | TAC | TTC | CAA | TGG | TTT | GTG | ACT | CTG | ACT | 1008 |
| 333 | T | P | P | C | A | Q | G | V | I | W | T | F | N | Q | T | T | 348 |
| 1009 | ACA | CCG | CCC | TGT | GCC | CAG | GGT | GTC | ATC | TGG | ACT | GTG | AAC | CAG | ACA | ACA | 1056 |

FIG._1B

```
349          V    M    L    S    A    K    Q    L    H    T    L    W         364
1057         GTG  ATG  CTG  AGT  GCT  AAG  CAG  CTC  CAC  ACC  CTC  GAC  ACC  CTG  TGG   1104

365          G    P    G    D    S    R    L    Q    N    F    R    A    T    Q    P   380
1105         GGA  CCT  GGT  GAC  TCT  CGG  CTA  CAG  AAC  TTC  CGA  GCG  ACG  CAG  CCT  1152

381          L    N    G    R    V    I    E    A    S    F    P    A    G    V    D    S   396
1153         TTG  AAT  GGG  CGA  GTG  ATT  GAG  GCC  TCC  TTC  CCT  GCT  GGA  GTG  GAC  AGC  1200

397          S    P    R    A    A    E    P    V    Q    L    N    S    C    L    A    A   412
1201         AGT  CCT  CGG  GCT  GCT  GAG  CCA  GTC  CAG  CTG  AAT  TCC  TGC  CTG  GCT  GCT  1248

413          G    D    I    L    A    L    V    F    G    L    L    F    A    V    T    S   428
1249         GGT  GAC  ATC  CTA  GCC  CTG  GTT  TTT  GGC  CTC  CTT  TTT  GCT  GTC  ACC  AGC  1296

429          V    A    F    L    V    Q    M    R    R    Q    H    R    R    G    T    K   444
1297         GTC  GCG  TTC  CTT  GTG  CAG  ATG  AGA  AGG  CAG  CAC  AGA  AGG  GGA  ACC  AAA  1344

445          G    G    V    S    Y    R    P    A    E    V    A    E    T    G    A    *   460
1345         GGG  GGT  GTG  AGC  TAC  CGC  CCA  GCA  GAG  GTA  GCC  GAG  ACT  GGA  GCC  TAG  1392

1393         AGG  CTG  GAT  CTT  GGA  GAA  TGT  CCT  GTC  CTG  CTC  ATT  ATG  CCA  CTT  CCT  TTT AAC  1440

1441         GGA  GCC  GGT  AAC  TGT  CCT  GTC  CTG  CTC  ATT  ATG  CCA  CTT  CCT  TTT  AAC  1488

1489         TGC  CAA  GAA  ATT  TTT  TAA  AAT  AAA  TAT  TTA  TAA  T    1522
```

```
   1 ggatcctgtt gactcgtgac cttaccccca acctgtgct ctctgaaaca tgagctgtgt
  61 ccactcaggg ttaaatggat taagggcggt gcaagatgtg ctttgttaaa cagatgcttg
 121 aaggcagcat gctcgttaag agtcatcacc aatccctaat ctcaagtaat caggacaca
 181 aacactgcgg aaggccgcag ggtcctctgc ctagaaaaac cagagacctt tgttcacttg
 241 tttatctgac cttcccctcca ctattgtcca tgaccctgcc aaatccccct ctgtgagaaa
 301 cacccaagaa ttatcaataa aaaaataaat ttaaaaaaaa aatacaaaaa aaaaaaaaaa
 361 aaaaaaaaaa gacttacgaa tagttattga taaatgaata gctattggta aagccaagta
 421 aatgatcata ttcaaaacca gacggccatc atcacagctc aagtctacct gatttgatct
 481 ctttatcatt gtcattcttt ggattcacta gattagtcat catcctcaaa atcctccccc
 541 aagttctaat tacgttccaa acatttaggg gttacatgaa gcttgaacct actacctttct
 601 ttgctttttga gccatgagtt gtaggaatga tgagtttaca cctacatgc tgggattaa
 661 tttaaacttt accctctaagt cagtgggta gcctttggct tatttttgta gctaattttg
 721 tagttaatgg atgcactgtg aatcttgcta tgatagtttt cctccacact ttgccactag
 781 gggtaggtag gtactcagtt ttcagtaatt gcttacctaa gaccctaagc cctattctc
 841 ttgtactggc ctttatctgt aatatgggca tatttaatac aatataattt ttgagttt
 901 tttgttttgtt tgttttgttg ttttttttgag acggagtctt gcatctgtca cctcccgagt tgcccaggct
 961 ggagtagcag tggtgccatc tcggctcact gcaagctcca cctcccgagt tcacgccatt
1021 ttcctgcctc agcctcccga gtagctggga ctacaggcgc ccgccaccat gcccggctaa
1081 tttttgtat tttgtgtaga cacgggtttt caccgtgtta gccagaatgg tctcgatctc
1141 ctgactcgt gatccaccccg cctcggcctc ccaaagttct gggattacag gtgtgagcca
1201 ccgcacctgg ccaatttttt gagtcttta aagtaaaaat atgtcttgta agctggtaac
1261 tatggtacat ttcctttttat tggtgccat ctgacggtca ttctctcttc tttgagttg
1321 gcatgcatat tctgacatt gctactttt gcagtccttt cattacattt attgaagag
1381 catgttatat ttaagcaaga tatgctaaga cacttggctt aaaaggttct ctcattagcc taacacagtg
1441 tcattgttgg taccacttgg atcataagtg atcataagt caagaaattg cacagtaata
1501 cttgtttgta agagggatga ttcaggtgaa tctgacacta agaaactccc ctacctgagg
1561 tctgagattc ctctgacatt gctgtatata ggctttcct ttgacagcct gtgactgcgg
1621 actatttc ttaagcaaga tatgctaaga tttgtgagc ctttttccag agagaggtct
1681 catatctgca tcaagtgaga acatataatg tctgcatgtt tccatattc aggaatgtt
1741 gcttgtttt tatgctttta tatagacagg gaaacttgtt cctcagtgac cttcctgagg
1801 tctgagattgt tattggatat catcattggc ccacgcttc tgaccttgga gtgactgcgg
1861 ggttcataat ctcaattctg tcagaattgg tacaagaaat agctgctatg tttcttgaca
1921 ttccacttgg taggaataa gaatgtgaaa ctcttcagtt ggtgtgtc cct?gtttt
```

FIG._2A

```
1981  ttgcaatttc  cttcttactg  tgttaaaaaa  aagtatgatc  ttgctctgag  aggtgaggca
2041  ttcttaatca  tgatctttaa  agatcaataa  tataatcctt  tcaaggatta  tgtcttatt
2101  ataataaaga  taatttgtct  ttaacagaat  caataatata  atcccttaaa  ggattatatc
2161  tttgctgggc  gcagtggctc  acacctgtaa  tcccagcact  ttgggtggcc  aaggtggaag
2221  gatcaaattt  gcctacttct  atattatctt  ctaaagcaga  attcatctct  cttccctcaa
2281  tatgatgata  ttgacaggt  ttgccctcac  tcactagatt  gtgagctcct  gctcagggca
2341  ggtagcgttt  tttgttttg  tttttgtttt  tcttttttga  gacagggtct  tgctctgtca
2401  cccaggccag  agtgcaatgg  tacagtctca  gctcactgca  gcctcaaccg  cctcggctca
2461  aaccatcatc  ccatttcagc  ctcctgagta  gctgggacta  gcctcactgca  ccattacacc
2521  tggctaattt  ttttgtattt  ctagtagaga  caggtttgg  ccatgttgcc  cgggctggtc
2581  tcgaactcct  ggactcaagc  aatccaccca  cctcagcctc  ccaaaatgag  ggacctggtc
2641  ttattcattt  ccatgtccct  agtcctatgc  agtccatagc  acctatggta  gtactaaata
2701  aatatttgtt  gaatgcaata  gtaaatagca  tttcaggag  caagaactag  attaacaaag
2761  gtggtaaaag  gtttggagaa  aaaaataata  gtttaatttg  gctagagtat  gaggagagt
2821  agtaggagac  aagatgaaa  ggtctctttgg  gcaaggttt  gaaggaagtt  ggaagtcaga
2881  agtacacaat  gtgcatatcg  tggcaggcag  tgggagcca  atgaaggctt  ttgagcagga
2941  gagtaatgtg  ttgaaaata  aatataggtt  aaacctatca  gagcccctct  gacacataca
3001  cttgcttttc  attcaagctc  aagtttgtct  cccacatacc  cattacttaa  ctcaccctcg
3061  ggctcccta  gcagcctgcc  ctacctcttt  acctgcttcc  tgtggagtc  agggatgtat
3121  acatgagctg  ctttccctct  cagccagagg  acatgggggg  cccagctcc  cctgccttc
3181  cccttctgtg  cctggagctg  ggaagcaggc  caggttagc  tgaggctggc  tgcaagctag
3241  ctgggtggtg  ccagggagag  cctgcatagt  gccaggtggt  gccttgggtt  ccaagctagt
3301  ccatgccccc  gataacccttc  tgcctgtgca  cacacctgcc  cctcactcca  ccccatcct
3361  agctttggta  tgggggagag  ggcacagggc  cagacaaacc  tgtgagactt  tggctccatc
3421  tctgcaaaag  gcgctctgt  gagtcagct  gctcccctcc  agcttgctc  ctcccccacc
3481  cagctctcgt  ttccaatgca  cgtacagccc  gtacacaccg  tgtgctggga  caccccACAG
3541  TCAGCCGCAT  GGCTCCCCTG  TGCCCCAGCC  CCTGGCTCCC  TCTGCTTGATC  CCGGCCCCTG
3601  CTCCAGGCCT  CACTGTGCAA  CTGCTGCTGT  CACTGCTGCT  TCTGTGCCT  GTCCATCCCC
3661  AGAGGTTGCC  CCGGATGCAG  GAGGATTCCC  CCTTGGGAGG  AGGCTCTTCT  GGGGAAGATG
3721  ACCCACTGGG  CGAGGAGGAT  CTGCCCAGTG  AAGAGGATTC  ACCCAGAGAG  GAGGATCCAC
3781  CCGGAGAGGA  GGATCTACCT  GGAGAGGAGG  ATCTACCTGG  AGAGGAGGAT  CTACCTGAAG
3841  TTAAGCCTAA  ATCAGAAGAA  CCCCAGAATA  TGAAGTTAGA  GGATCTACCT  ACTGTTGAGG
3901  CTCCTGGAGA  TCCTCAAGAA  ATGCCCACAG  ATGCCCACAG  GGACAAAGAA  Ggtaagtggt
```

```
3961  catcaatctc  caaatccagg  ttcatgactc  ttcatgactc  cccagccta
4021  ggctctgttc  actcagggaa  ggaggggaga  ctgtactccc  cttccagagg
4081  tcccatacca  atatccccat  ccccactctc  ggaggtagaa  gtggagagaa
4141  aataaaaagg  gtgcaaaagg  agagagtga  gctggatgag  aggggaggc
4201  tggagaagag  aagggatga  gaactgcaga  tgagagaaaa  cagagaaaa
4261  aaataggtgg  agaaggagag  tcagagagtt  tgaggggaag  agcttgggag
4321  gtgaagtggg  taccagagaa  agcaagaaag  agctgtaga  tcttaggcta
4381  caatgaggaa  ttgagaccta  acacagcagg  agtcatctca  tgctttcttg
4441  actcccaagc  caggaatttg  ggaaggaagg  tagagaaacg  agggatgagt
4501  ggggagaaga  aagaagggag  aaaggaaaga  tacaaggcag  gactcaggac
4561  actcccgcc  actcacttct  tttttttttt  ttggagacca  tttgttgcc
4621  tgaagtgccc  actcacttct  tttttttttt  actcatttgg  cgggttcaag
4681  caggctggag  tgcaatggcg  cgatctcggc  tcactgcaac  gccaccacgc
4741  tgattctcct  gcctcagcct  ctagtgcgc  agctgcgatt  aggctggtct
4801  ccggctaatt  tttgtatttt  tagtagagac  ggggtttcgc  catgttggtc  ggattatagg
4861  cgaactcctg  atctcaggtg  atccaaccac  cctggcctcc  caaagtgctg  aagacaatga
4921  cgtgagccac  cgcgcctggc  ctgaagcagc  cactcacttt  tacagaccct  tgggtgcgg
4981  ttgcaagctg  gtaggattgc  tgttttggcc  acccagctgc  ggtgttgagt  ctcctgtaag
5041  tctcctgtgc  tttgcacctg  gcccgcttaa  ggcatttgtt  acccgtaatg  taagcttgag
5101  gcatctgcgt  ttgtgacatc  gttttggtcg  ccaggaaggg  attggggctc  TGGAGgtgag
5161  cggttcatcc  tttttcattta  tacagGGGAT  GACCAGAGTC  ATTGGCGCTA  cccctacagc
5221  acacccaccc  gctgcacaga  cccaatctgg  gaacccagct  ctgtggatct  cccctcacct
5281  cgtccctgaa  cactgtccca  gggcgtccca  cccgccgccc  accgtcccac  tatactctcc
5341  tttctacccg  ggttccctaa  gttcctgacc  taggcgtcag  acttcctcag  GCTTCCAGTC
5401  caccccagGC  GACCCGCCCT  GGCCCCAGCC  GTCCCCAGCC  TGCGCGGGCC  CCCTGAACT
5461  CCCGGTGGAT  ATCCGCCCCC  AGCTCGCCGC  CTTCTGCCCG  GCCCTGCGCC  GCCACAGTGg
5521  CCTGGGCTTC  CAGCTCCCGC  CGCTCCCAGA  ACTGCGCCTG  CGCAACAATG  ggaaccgtcg
5581  tgagggggtc  tccccgccga  gacttgggga  tgggcggggg  cgcaggggaag  ggaaccgtcg
5641  cgcagtgcct  gcccgggggt  tgggctggcc  ctaccgggcg  gggccggctc  acttgcctct
5701  cctacgcag  TGCAACTGAC  CCTGCCTCCT  GGGCTAGAGA  TGGGCTCTGGG  TCCCGGGCGG
5761  GAGTACCGGG  CTCTGCAGCT  GCATCTGCAC  TGGGGGGCTG  CAGGCTCGTCC  GGGCTCGGAG
5821  CACACTGTGG  AAGGCCACCG  TTTCCCTGCC  GAGtgagcg  cggactgccc  gagaagggc
5881  aaaggagcgg  ggcggacggg  AGCACCGCCT  TTGCCAGAGT  TGACGAGGCC  tgtcctttc
5881  agATCCACGT  GGTTCACCTC  AGCACCGCCT  TTGCCAGAGT  TGACGAGGCC  TTGGGGCGCC
```

FIG._2D

```
5941 CGGGAGGCCT GGCCGTGTTG GCCGCCTTTC TGGAGgtacc agatcctgga caccccctac
6001 tcccgcttt cccatcccat gctcctcccg gactctatcg tggagccaga gacccatcc
6061 cagcaagctc actcagccc ctggctgaca aactcattca cgcactgttt gttcatttaa
6121 cacccactgt gaaccaggca ccagccccca acaaggattc tgaagctgta ggtccttgcc
6181 tctaaggagc ccacagccag tggggaggc tgacatgaca gacacatagg aaggacatag
6241 taaagatggt ggtcacagag gaggtgacac ttaaagcctt cactggtaga aagaaaagg
6301 aggtgttcat tgcagaggaa acagaatgtg caaagactca gaatatggcc tatttaggga
6361 atggctacat acaccatgat tagaggaggc ccagtaaagg gaagggatgg tgagatgcct
6421 gctaggttca ctcactcact tttatttatt tttgacagtc tctctgtcgc
6481 ccaggctgga gtgcagtggt gtgatcttgg gtcactgcaa cttccgcctc ccgggttcaa
6541 gggattctcc tgcctcagct tcctgagtag ctggggttac aggtgtgtgc caccatgccc
6601 agctaatttt tttttgtatt tttagtagac agggtttcac catgttggtc agctggtct
6661 caaactcctg gcctcaagtg atccgcctga ctcagcctac caaagtgctg attacaagtg
6721 tgagccaccg tgcccagcca cactcactga ttctttaatg ccagccacac agcacaaagt
6781 tcagagaaat gcctccatca tagcatgtca atatgttcat actctttaggt tcatgatgtt
6841 cttaacatta ggttcataag caaaataaga aaaaagaata ataaataaaa gaagtggcat
6901 gtcaggacct cacctgaaaa gccaaacaca gaatcatgaa ggtgaatgca gaggtgacac
6961 caacacaaag gtgtatatat ggtttcctgt ggggagtatg tacggaggca gcagtgagtg
7021 agactgcaaa cgtcagaagg gcacggtca ctgagagcct agtatcctag taaagtgggc
7081 tctctccctc tctctccagc ttgtcattga aaaccagtcc accaagcttg ttggttcgca
7141 cagcaagagt acatagagtt tgaaataata cataggattt taagagggag acactgtctc
7201 taaaaaaaaa aacaacagca acaacaaaaa gcaacaacca ttacaattt atgttccctc
7261 agcattctca gagctgagaa atgggagagg actatgggaa cccccttcat gttccggcct
7321 tcagccatgg ccctggatac atgcactcat ctgtcttaca atgtcattcc cccagGAGGG
7381 CCCGGAAGAA AACAGTGCCT ATGAGCAGTT GCTGTCTCGC TTGAAGAAA TCGCTGAGGA
7441 AGtcagttt gttggtctgg ccactaatct ctgtggccta gttcataaag aatcaccctt
7501 tggagttca ggtctgaggc tggagatggg ctcccctccag tgcaggaggg attgaagcat
7561 gagccagcgc tcatcttgat aataaccatg aagctgacag acacagttac ccgcaaacgg
7621 ctgcctacag attgaaaacc aagcaaaac cgcgggcac ggtggctcac gcctgtaatc
7681 ccagcacttt gggaggccaa ggcaggtgtc tcacgaggtc aagagatcaa gaccatcctg
7741 gccaacatgg tgaaacccca tctctactaa aaatacgaaa aaatagccag gcgtggtggc
7801 gggtgcctgt aatcccagct actcgggagg ctgaggcagg agaatgcat gaacccggga
7861 ggcagaagtt gcagtgagcc gagatcgtgc cactgcactc cagcctgggc aacagagcga
```

```
7921  gactcctgtc  tcaaaaaaaa  aaaaaaaaaa  gaaaaccaag  caaaaaccaa  aatgagacaa
7981  aaaaaacaag  accaaaaaat  ggtgtttgga  aattgtcaag  gtcaagtctg  gagagctaaa
8041  cttttcctga  gaactgttta  tctttaataa  gcatcaaata  tttaacttt   gtaaatactt
8101  ttgttggaaa  tcgttctctt  cttagtcact  ctttgggtcat tttaaatctc  acttactcta
8161  ctagacctt   taggtttctg  ctagactagg  tagaactctg  cctttgcatt  tcttgtgtct
8221  gttttgtata  gttatcaata  ttcatatttta ttttacaagtt attcagatca  ttttttcttt
8281  tcttttttt   tttttttttt  ttttttacat  ctttagtaga  gacagggttt  caccatattg
8341  gccaggctgc  tctcaaactc  ctgacccttgt gatccaccag  cctcggcctc  ccaagtgct
8401  gggattcatt  tttttcttt   aatttgctct  gggcttaaac  ttgtggccca  gcacttatg
8461  atggtacaca  gagttaagag  tgtagactca  gacggtcttt  cttccttcct  tctcttcctt
8521  cctccctcc   ctcccacctt  cccttctctc  cttcctttct  ttcttcctct  cttgcttcct
8581  caggcctctt  ccagttgctc  caaagccctg  tacttttttt  tgagttaacg  tcttatggga
8641  agggcctgca  cttagtgaag  aagtggtctc  agagttgagt  tacccttggct tctgggaggt
8701  gaaactgtat  ccctataccc  tgaagcttta  aggggtgca   atgtagatga  gacccaaca
8761  tagatcctct  tcacagGCTC  AGAGACTCAG  GTCCCAGGAC  TGGACATATC  TGCACTCCTG
8821  CCCTCTGACT  TCAGCCGCTA  CTTCCAATAT  GAGGGTCTC   TGACTACACC  GCCCTGTGCC
8881  CAGGGTGTCA  TCTGGACTGT  GTTTAACCAG  ACAGTGATGC  TGAGTGCTAA  GCAGtgggc
8941  ctggggtgtg  tgtggacaca  gtgggtgcgg  gggaaagagg  atgtaagatg  agatgagaaa
9001  caggagaaga  aagaaatcaa  ggctgggctc  tgtgcttac   gcctataatc  ccaccacgtt
9061  gggaggctga  ggtgggagaa  tggtttgagc  ccaggagttc  aagacaaggc  gggcaacat
9121  agtgtgaccc  catctctacc  aaaaaaaacc  caacaaaaacc aaaaatagcc  gggcatggtg
9181  gtatgcggcc  tagtcccagc  tactcaagga  ggctgaggtg  ggaagatgc   ttgattccag
9241  gagtttgaga  ctgcagtgag  ctatgatccc  accactgcct  accatcttta  ggatacattt
9301  atttattat   aaaagaaatc  aagagaagcc  atgggaata   caggagctgg  agggtggagc
9361  cctgagggtgc tggttgtgag  ctggcctgag  acccttgttt  cctgtcatgc  catgaaccca
9421  cccacactgt  ccactgacct  ccctagCTCC  ACACCCTCTC  TGACACCCTG  TGGGGACCTG
9481  GTGACTCTCG  GCTACAGCTG  AACTTCCGAG  CGACGCAGCC  TTTGAATGGG  CGAGTGATTG
9541  AGGCCTCCTT  CCCTGCTGGA  GTGGACAGCA  GTCCTCGGGC  TGCTGAGCCA  Ggtacagctt
9601  tgtctggttt  ccccccagcc  agtagtcct   tatcctccca  tgtgtgtgcc  agtgtctgtc
9661  attggtggtc  acagcccgcc  tctcacatct  cctttttctc  tccagTCCAG  CTGAATTCCT
9721  GCCTGGCTGC  TGgtgagtct  gccctctctc  ttgtcctga   tgccaggaga  ctcctcagca
9781  ccattcagcc  ccagggctgc  tcaggaccgc  ctctgctccc  tctcctttc   tgcagaacag
9841  accccaaccc  caatattaga  gaggcagatc  atggtgggga  ttccccccatt gtcccccagag
```

FIG._2E

```
 9901 gctaattgat tagaatgaag cttgagaaat ctcccagcat ccctctcgca aaagaatccc
 9961 ccccctttt tttaaagata gggtctcact ctgtttgccc caggctgggg tgttgtggca
10021 cgatcatagc tcactgcagc ctcgaactcc taggctcagg caatccttc acctagctt
10081 ctcaaagcac tgggactgta ggcatgagcc actgtgcctg gcccaaacg gcccttttac
10141 ttggcttta ggaagcaaaa acggtgctta tcttaccct tctcgtgtat ccaccctcat
10201 cccttggctg gcctctcctg gagactgagg cactatgggg ctgcctgaga actcggggca
10261 ggggtggtgg agtgcactga ggcaggtgtt gaggaactct gcagacccct cttccttccc
10321 aaagcagccc tctctgctct ccatcgcagG TGACATCCTA GCCCTGGTTT TTGGCCTCCT
10381 TTTTGCTGTC ACCAGCGTCG CGTTCCTTGT GCAGAGATGAGA AGGCAGCACA Gtattacac
10441 tgacccttc ttcaggcaca agcttccccc acccttgtgg agtcacttca tgcaaagcgc
10501 atgcaaatga gctgctcctg ggccagtttt ctgattagcc tttcctgttg tgtacacaca
10561 gAAGGGGAAC CAAAGGGGGT GTGAGCTACC GCCCAGCAGA GGTAGCCGAG ACTGGAGCCT
10621 AGAGGCTGGA TCTTGGAGAA TGTGAGAAGC CAGCCAGAGG CATCTGAGGG GGAGCCGGTA
10681 ACTGTCCTGT CCTGCTCATT ATGCCACTTC CTTTTAACTG CCAAGAAATT TTTTAAAATA
10741 AATATTTATA ATaaaatatg tgttagtcac cttgttccc caaatcagaa ggagtattt
10801 gaatttccta ttactgttat tagcaccaat ttagtggtaa tgcatttatt ctattacagt
10861 tcggcctcct tccacacatc actccaatgt gttgctcc
```

*FIG._2F*

| FIG._2A |
| FIG._2B |
| FIG._2C |
| FIG._2D |
| FIG._2E |
| FIG._2F |

*FIG._2*

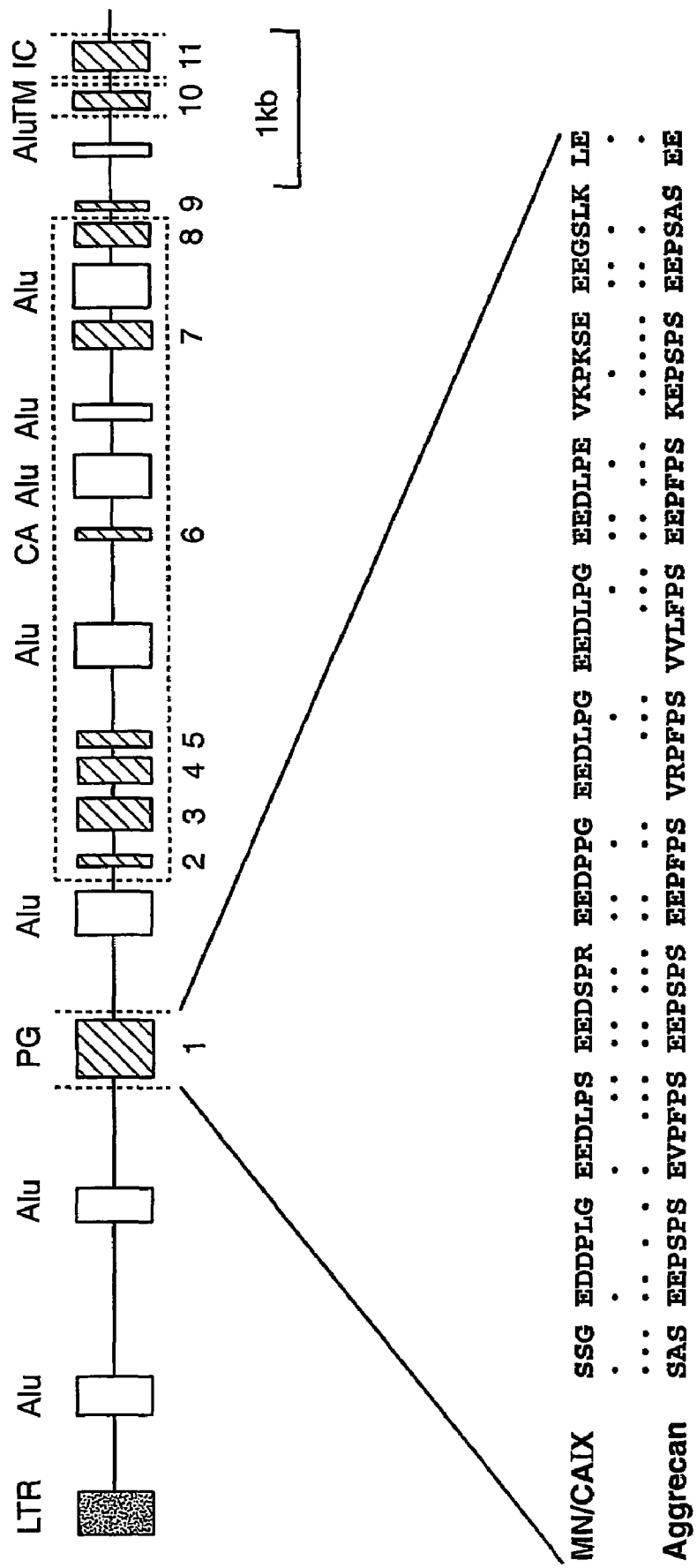
FIG._3

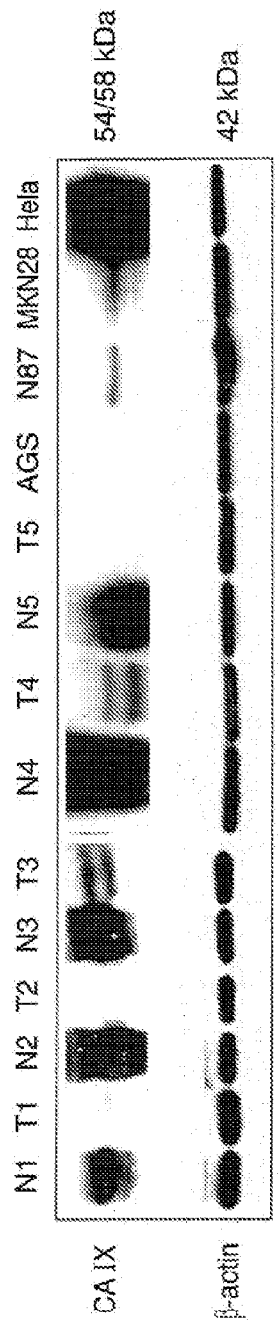
FIG._4A
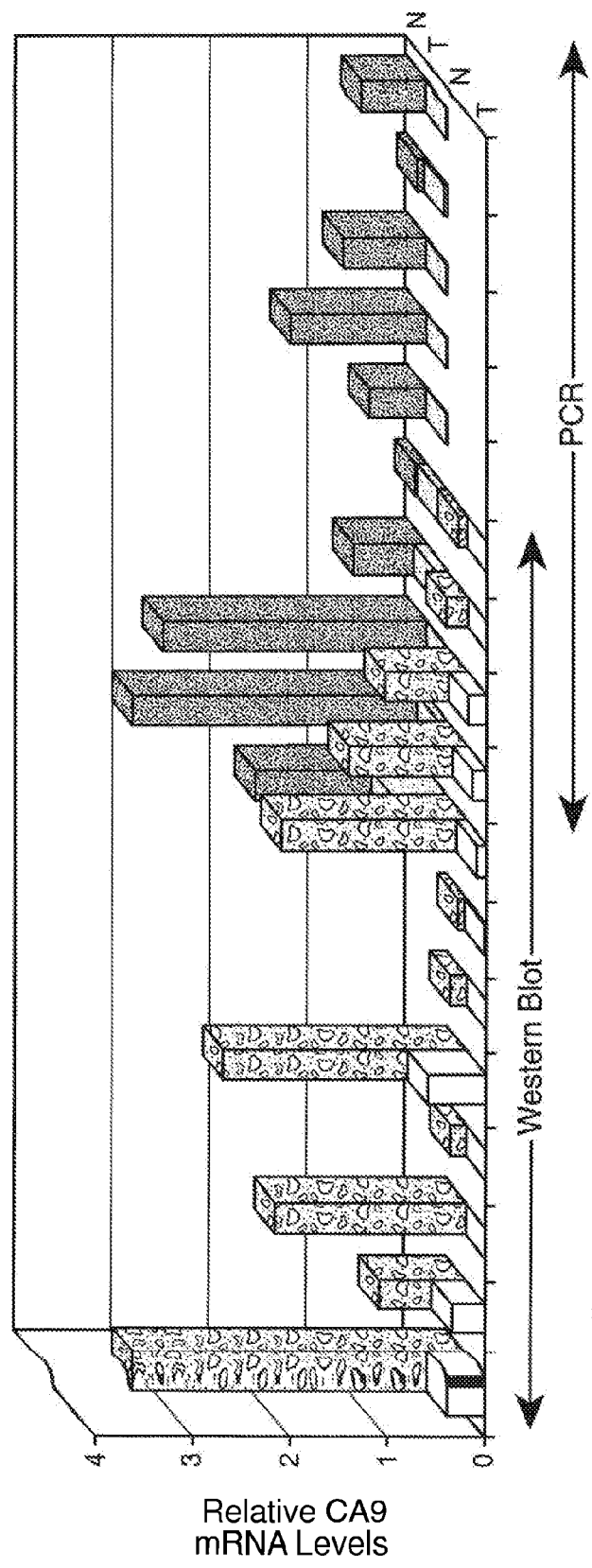
FIG._4B

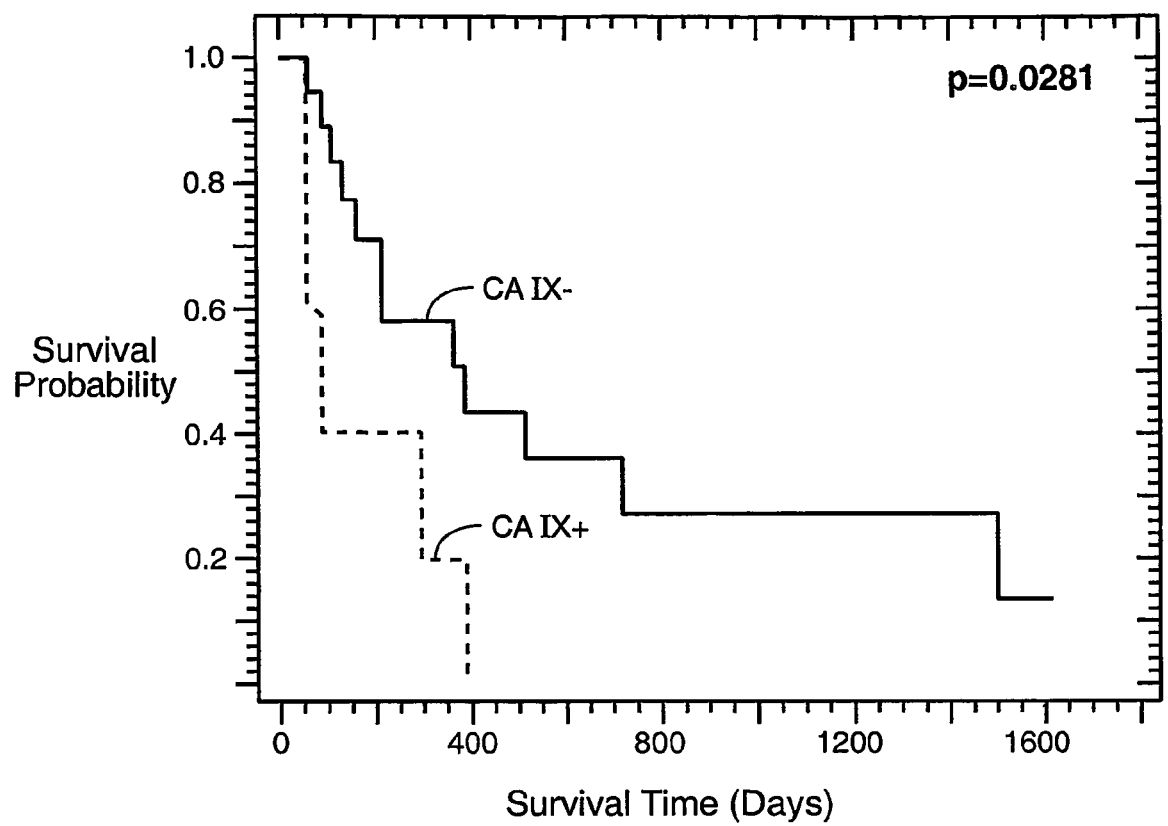
FIG._5

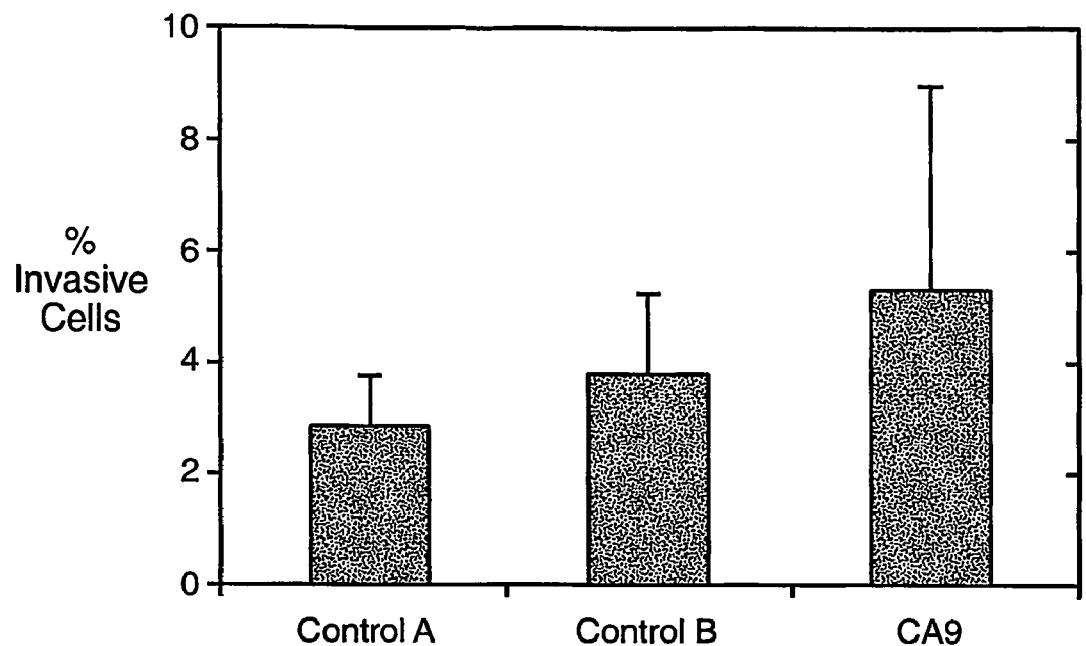
FIG._6A
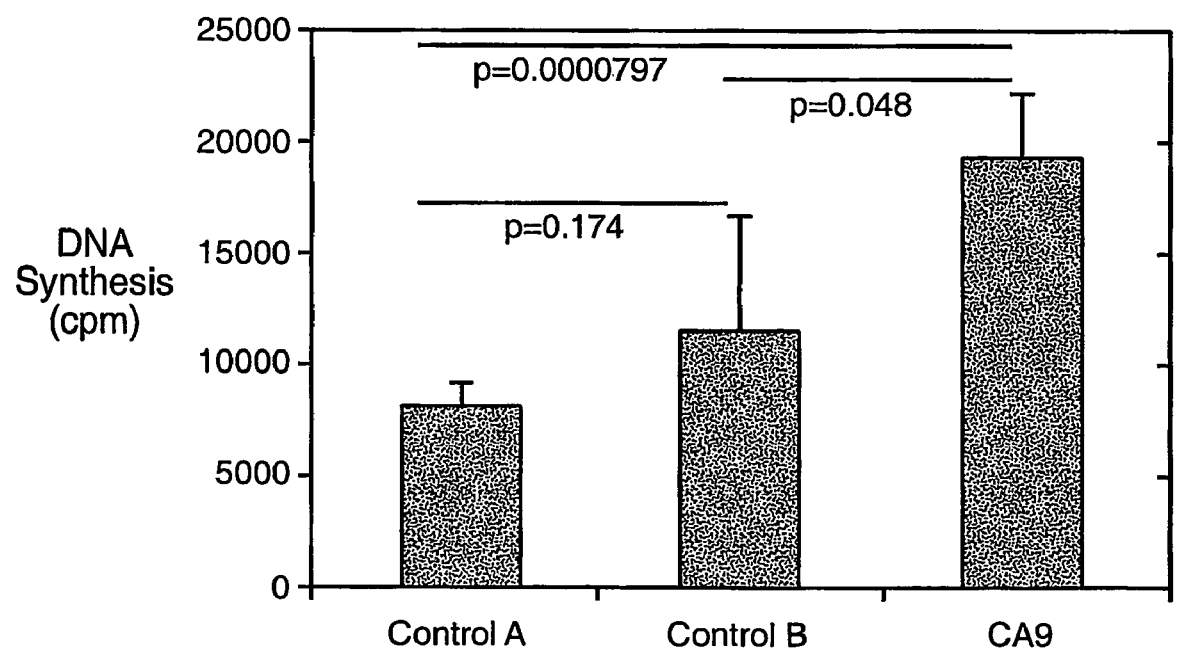
FIG._6B

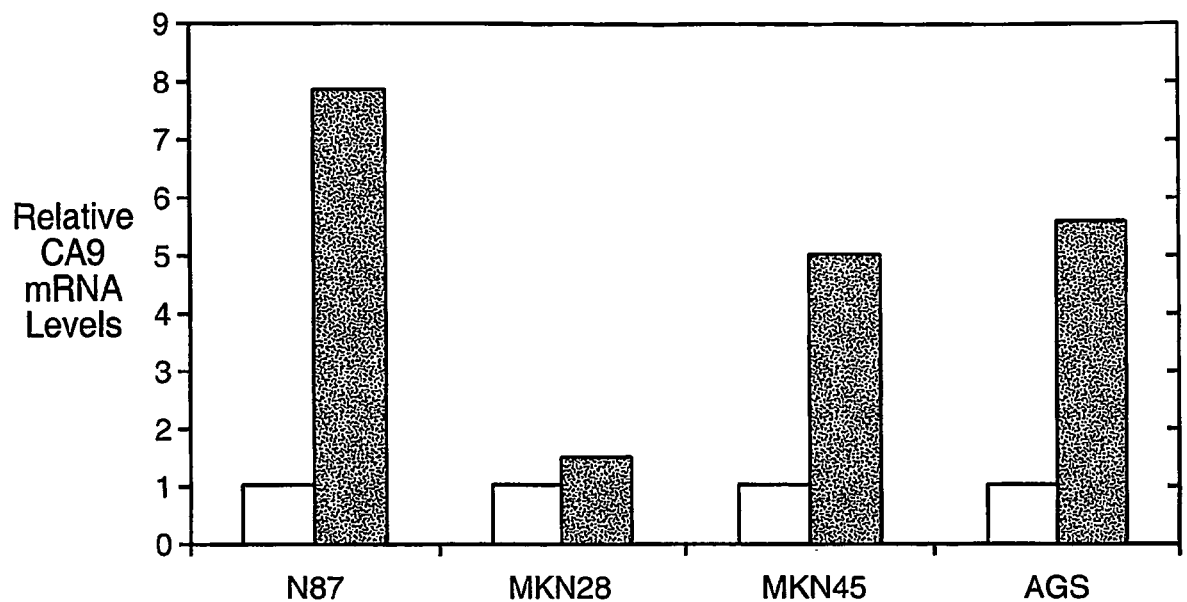
FIG._7A
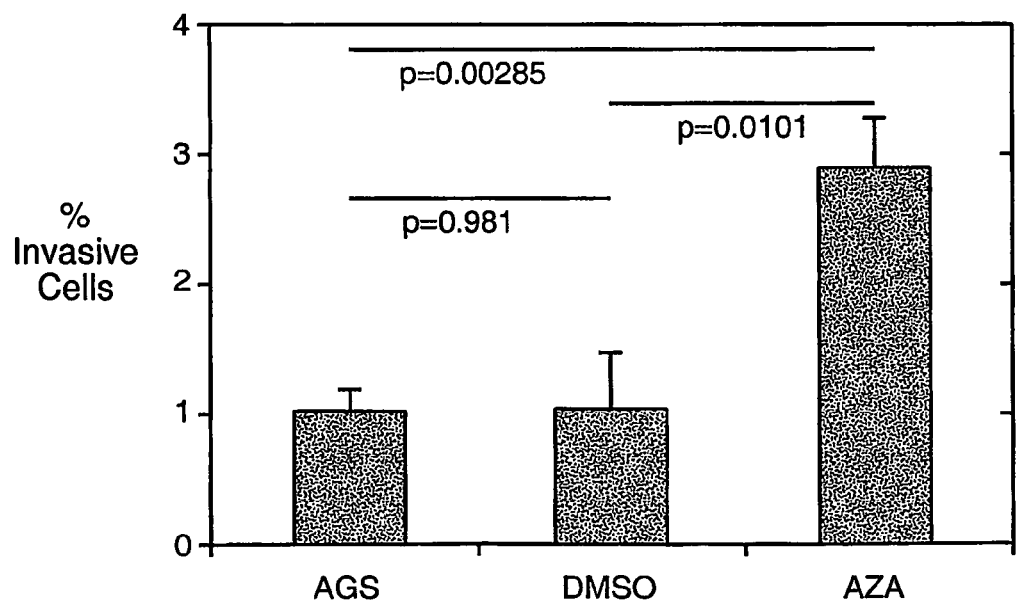
FIG._7B

MN/CA IX AND CANCER PROGNOSIS

FIELD OF THE INVENTION

The present invention is in the general area of medical genetics and in the fields of biochemical engineering, immunochemistry and oncology. More specifically, it relates to the MN gene—a cellular gene considered to be an oncogene, known alternatively as MN/CA9, CA9, or carbonic anhydrase 9, which gene encodes the oncoprotein now known alternatively as the MN protein, the MN/CA IX isoenzyme, MN/CA IX, carbonic anhydrase IX, CA IX or the MN/G250 protein.

More specifically, the instant invention is directed to the identification of MN antigen or MN gene expression in patient samples, which provides the basis for diagnostic/prognostic assays for cancer and for making clinical decisions on cancer treatment. Still more specifically, the instant invention concerns methods which are prognostic for patients with a preneoplastic/neoplastic disease, wherein said disease affects a tissue, which normally expresses MN protein, but wherein said tissue loses or has significantly reduced MN expression upon carcinogenesis. Gastric cancer is exemplary of such a neoplastic disease.

BACKGROUND

As indicated above, the MN gene and protein are known by a number of alternative names, which names are used herein interchangeably. The MN protein was found to bind zinc and have carbonic anhydrase (CA) activity and is now considered to be the ninth carbonic anhydrase isoenzyme—MN/CA IX or CA IX [4]. According to the carbonic anhydrase nomenclature, human CA isoenzymes are written in capital roman letters and numbers, whereas their genes are written in italic letters and arabic numbers. Alternatively, "MN" is used herein to refer either to carbonic anhydrase isoenzyme IX (CA IX) proteins/polypeptides, or carbonic anhydrase isoenzyme 9 (CA9) gene, nucleic acids, cDNA, mRNA etc. as indicated by the context.

The MN protein has also been identified with the G250 antigen. Uemura et al. [35] states: "Sequence analysis and database searching revealed that G250 antigen is identical to MN, a human tumor-associated antigen identified in cervical carcinoma (Pastorek et al., 1994)."

Zavada et al., International Publication Number WO 93/18152 (published Sep. 16, 1993) and U.S. Pat. No. 5,387,676 (issued Feb. 7, 1995), describe the discovery of the MN gene and protein. The MN gene was found to be present in the chromosomal DNA of all vertebrates tested, and its expression to be strongly correlated with tumorigenicity. In general, oncogenesis may be signified by the abnormal expression of CA IX protein. For example, oncogenesis may be signified: (1) when CA IX protein is present in a tissue which normally does not express CA IX protein to any significant degree; (2) when CA IX protein is absent from a tissue that normally expresses it; (3) when CA9 gene expression is at a significantly increased level, or at a significantly reduced level from that normally expressed in a tissue; or (4) when CA IX protein is expressed in an abnormal location within a cell.

The MN protein is now considered to be the first tumor-associated carbonic anhydrase isoenzyme that has been described. The carbonic anhydrase family (CA) includes eleven catalytically active zinc metalloenzymes involved in the reversible hydration-dehydration of carbon dioxide: $CO_2 + H_2O \Leftrightarrow HCO_3^- + H^+$. CAs are widely distributed in different living organisms. The CAs participate in a variety of physiological and biological processes and show remarkable diversity in tissue distribution, subcellular localization, and biological functions [1, 2, 27]. Carbonic anhydrase IX, CA IX, is one of the most recently identified isoenzymes [3, 4]. Because of the CA IX overexpression in transformed cell lines and in several human malignancies, it has been recognized as a tumor-associated antigen and linked to the development of human cancers [5-7].

CA IX is a glycosylated transmembrane CA isoform with a unique N-terminal proteoglycan-like extension [4]. Through transfection studies it has been demonstrated that CA IX can induce the transformation of 3T3 cells [4]. Recent studies have revealed that CA IX not only participates in cell adhesion, but also can be induced in hypoxia via the HIF-1 protein binding to the hypoxia-responsive element of the MN promoter [8, 9]. The transcription of the MN gene is negatively regulated by the von Hippel-Lindau tumor suppressor gene in renal cell carcinoma cells [28]. The protein product of the von Hippel-Lindau tumor suppressor gene interacts with the ubiquitin ligase complex that is responsible for targeting HIF-1α for oxygen-dependent proteolysis [29, 30]. Thus, low levels of oxygen lead to stabilization of HIF-1α, which in turn leads to the increased expression of MN [9]. Areas of high expression of MN in cancers are linked to tumor hypoxia as reported in many cancers and incubation of tumor cells under hypoxic conditions leads to the induction of MN expression [9-14].

Many studies have confirmed the diagnostic/prognostic utility of MN, using the MN-specific monoclonal antibody (MAb) M75 in diagnosing/prognosing precancerous and cancerous cervical lesions [6, 37, 38, 39, 55]. Immuno-histochemical studies with the M75 MAb of cervical carcinomas and a PCR-based (RT-PCR) survey of renal cell carcinomas have identified MN expression as closely associated with those cancers and indicates that MN has utility as a tumor biomarker [6, 36, 38]. In various cancers (notably uterine cervical, ovarian, endometrial, renal, bladder, breast, colorectal, lung, esophageal, head and neck and prostate cancers, among others), CA IX expression is increased and has been correlated with the microvessel density and the levels of hypoxia in some tumors [10, 11].

In tissues that normally do not express MN protein, CA IX positivity is considered to be diagnostic for preneoplastic/neoplastic diseases, such as, lung, breast and cervical cancers [12-14]. However, among those cancerous tissues, higher MN expression often indicates a better prognosis. Previous studies have reported that there is an inverse correlation between CA IX expression and stage and grade in some tumors, including clear cell RCC [40], cervical carcinoma [39], colorectal tumors [7], and esophageal cancer [52]. Of these studies, the three that were non-RCC-related found that low expression of CA IX correlated with poor prognostic factors, such as lymph node metastases and depth of invasion. Bretheau et al. 1995 [41] reported the poor prognosis of RCC patients with high grade and stage tumors, which according to Uemura et al. [40] would be expected to express CA IX at lower levels. Bui et al. [42; International Publication No. WO 03/089659] reported that "low" CA IX ($\leq 85\%$) staining was an independent poor prognostic factor for survival for patients with metastatic RCC.

Very few normal tissues have been found to express MN protein to any significant degree; those MN-expressing normal tissues include the human gastric mucosa and gallbladder epithelium, and some other normal tissues of the alimentary tract [45, 15, 16]. Immunohistochemical analysis of the normal large intestine revealed moderate CA IX staining in the proximal colon, with the reaction becoming weaker distally.

The staining was confined to the basolateral surfaces of the cryptal epithelial cells, the area of greatest proliferative capacity. As CA IX is much more abundant in the proliferating cryptal epithelium than in the upper part of the mucosa, it may play a role in control of the proliferation and differentiation of intestinal epithelial cells. Cell proliferation increases abnormally in premalignant and malignant lesions of the colorectal epithelium, and therefore, is considered an indicator of colorectal tumor progression. [43, 44]. Interestingly, CA9 deficient mice develop gastric hyperplasia which is associated with increased proliferation [17], raising the question, whether the putative pathophysiological role of CA IX in gastric cancer development and progression is different from the one observed in cancers of non-gastric origin.

Gastric cancer is the second most common cause of cancer-related deaths worldwide [22, 23]. Despite its decreasing incidence it remains a great challenge for clinicians and oncologists. In recent years various groups have analysed the genetic and molecular changes leading to gastric cancer. Those changes include, among others, the overexpression of oncogenes, such as growth factor receptors K-sam and c-met, the loss of certain tumor suppressor genes, such as APC and p53, as well as alteration of adhesion molecules, including E-cadherin and the catenins [22-26]. Recently, the group of carbonic anhydrases and especially CA IX have received increasing attention [2]. However, studies to date investigating CA IX expression in gastric mucosa, which normally overexpresses CA IX, have provided only diagnostic analysis, associating the presence of gastric cancer with diminished levels of CA IX or loss of CA IX.

Disclosed herein is a surprising finding that has led to novel and inventive prognostic methods for gastric cancer and related cancers, that are diagnosed by the loss or reduction of the CA IX expression, that is abundant in corresponding normal tissue. Surprisingly, among such cancers, it was found that CA IX expression that is higher than the absent or significantly reduced levels of CA IX expression considered diagnostic for gastric and related cancers, indicates a poorer prognosis for patients that have been diagnosed with such cancers, particularly when such higher CA IX expression is found at the invasion fronts of such cancers. Disclosed herein is the surprising finding that in gastric cancer and related cancers, a higher expression of CA IX indicates a poorer prognosis for afflicted patients, particularly when expressed at the invasion front of the cancer.

SUMMARY OF THE INVENTION

The present invention relates to prognostic methods comprising quantitating levels of MN/CA9 gene expression products in patients afflicted with preneoplastic/neoplastic diseases of tissues, wherein the normal tissue associated with such a preneoplastic/neoplastic disease expresses CA IX, but loses CA IX expression upon carcinogenesis. Quantitating such levels of MN/CA9 gene expression product is useful in determining prognosis of the patient. Such tissue is preferably selected from the group consisting of gastric mucosa, gallbladder, biliary ducts, ductal cells of duodenal glands, testis including ductular efferens and rete testis, ovary including surface coelomic epithelium and rete ovarii, basal cells of hair follicles, and central nervous system choroid plexus. More preferably, said tissue is gastric mucosa, gallbladder, biliary ducts or ductal cells of duodenal glands; still more preferably, said tissue is gastric mucosa, gall bladder or biliary ducts; further preferably said tissue is gastric mucosa.

A first prognostic method comprises quantitating the level of a MN/CA9 gene expression product in a tissue sample taken from a patient, and comparing that level with levels of MN/CA9 gene expression products in comparable tissue samples from patients afflicted with the same disease. A second prognostic method comprises analyzing the tissue sample from the invasion front of said preneoplastic/neoplastic disease in said patient and comparing the MN/CA9 gene expression level to the levels normally found in said tissue. In addition to predicting clinical outcome, the methods of the present invention also identify high-risk patients in need of adjuvant therapy, and/or CA IX-targeted therapies, among other courses of treatment.

In one aspect, the invention concerns methods which are prognostic for a preneoplastic/neoplastic disease afflicting a subject vertebrate, preferably a mammal, wherein said disease affects a tissue, which tissue normally expresses MN/CA IX protein, but loses or has significantly reduced MN/CA IX expression upon carcinogenesis, said method comprising:

(a) detecting MN/CA9 gene expression product in a sample comprising preneoplastic/neoplastic tissue taken from said vertebrate, (b) quantitating the level of said MN/CA9 gene expression product in said sample, (c) comparing the level of MN/CA9 gene expression product of step (b) to the average level of MN/CA9 gene expression product in comparable samples taken from vertebrates afflicted by the same preneoplastic/neoplastic disease as the subject vertebrate, and (d) determining that said subject vertebrate has a poorer prognosis if the level of MN/CA9 gene expression product of step (b) is higher than the average level of MN/CA9 gene expression product in said comparable samples;

wherein said MN/CA IX protein is encoded by a nucleotide sequence selected from the group consisting of:

(1) SEQ ID NO: 1's coding region;

(2) nucleotide sequences that hybridize under stringent hybridization conditions of 50% formamide at 42 degree C. to complement of SEQ ID NO: 1's coding region; and (3) nucleotide sequences that differ from SEQ ID NO: 1's coding region or from the nucleotide sequences of (2) in codon sequence due to the degeneracy of the genetic code.

Preferred assays to be used according to the methods of the invention to detect said MN/CA9 gene expression product in detecting step (a) are those wherein said MN/CA9 gene expression product comprises an MN/CA IX protein or MN/CA IX polypeptide, and said assays are selected from the group consisting of Western blots, enzyme-linked immunosorbent assays, radioimmunoassays, competition immunoassays, dual antibody sandwich assays, immunohistochemical staining assays, agglutination assays, fluorescent immunoassays, and cytofluorometry. More preferably, said MN/CA9 gene expression product detecting step (a) is by immunohistochemical staining, and said quantitating step (b) comprises determining the percentage of immunoreactive cells and/or the intensity of immunostaining of immunoreactive cells, preferably comprising the addition or multiplication of said percentage of immunoreactive cells and said intensity of immunostaining of immunoreactive cells. Still more preferably, said detecting step (a) comprises the use of the MN-specific M75 monoclonal antibody secreted by the hybtidoma VU-M75 which has Accession No. ATCC HB 1128.

In a preferred embodiment of the invention, the MN/CA9 gene expression product is CA IX antigen, and the CA IX antigen is quantitated in preneoplastic/neoplastic vertebrate samples, preferably mammalian samples, more preferably human samples. Such preneoplastic/neoplastic samples can be tissue specimens, tissue extracts, cells, cell lysates and cell extracts, among other samples. Such tissue specimens can be variously maintained, for example, they can be fresh, frozen, or formalin-, alcohol- or acetone- or otherwise fixed and/or paraffin-embedded and deparaffinized. Preferred tissue samples are formalin-fixed, paraffin-embedded tissue samples or frozen tissue samples. In a preferred embodiment, the disease is gastric cancer, and the sample is taken from the invasion front of the gastric cancer. Preferably, said sample is taken from the invasion front of said preneoplastic/neoplastic disease, preferably a neoplastic disease, and said comparable samples used in comparing step (c) are analogous invasion front samples.

An exemplary and preferred method which is prognostic for a preneoplastic/neoplastic disease affecting a subject vertebrate, wherein said disease affects a tissue, which tissue normally expresses MN/CA IX protein, but loses or has significantly reduced MN/CA IX expression upon carcinogenesis, comprises:

(a) detecting MN/CA9 gene expression product in a sample comprising preneoplastic/neoplastic tissue taken from said vertebrate, said detecting comprising immunohistochemical staining with MN/CA IX-specific antibody to detect MN/CA IX protein in the sample;

(b) quantitating the level of said MN/CA9 gene expression product in said sample, comprising:

(b1) determining the percentage of immunoreactive cells, wherein the percentage of immunoreactive cells is assigned
  a value of 0 if no immunoreactive cells,
  a value of 1 if less than 10% immunoreactive cells,
  a value of 2 if between 11% and 50% immunoreactive cells, or
  a value of 3 if more than 50% immunoreactive cells;

(b2) determining the intensity of immunostaining of the immunoreactive cells, wherein the intensity of MN/CA IX immunostaining is assigned
  a value of 0 for staining equal to a negative control,
  a value of 1 for weak staining,
  a value of 2 for moderate staining, or
  a value of 3 for strong staining; and (b3) adding the value for the percentage of immunoreactive cells found in step (b1) and the value for the intensity of immunostaining found in step (b2) to obtain the immunoreactivity score;

(c) comparing the immunoreactivity score of the subject vertebrate found in step (b) to the average immunoreactivity score in comparable samples taken from vertebrates afflicted by the same preneoplastic/neoplastic disease as the subject vertebrate, comprising determining the immunoreactivity scores of said comparable samples analogously to the determination of the immunoreactivity score of the sample from the subject vertebrate in steps (b1) to (b3), and averaging said immunoreactivity scores from said comparable samples; and (d) determining that said subject vertebrate has a poorer prognosis if said immunoreactivity score of the sample determined in steps (b1) to (b3) is above the average immunoreactivity score of said comparable samples found in step (c);

wherein said MN/CA IX protein is encoded by a nucleotide sequence selected from the group consisting of:

(2) SEQ ID NO: 1's coding region;

(2) nucleotide sequences that hybridize under stringent hybridization conditions of 50% formamide at 42 degree C. to complement of SEQ ID NO: 1's coding region; and (3) nucleotide sequences that differ from SEQ ID NO: 1's coding region or from the nucleotide sequences of (2) in codon sequence due to the degeneracy of the genetic code.

In an alternative preferred embodiment, preferred assays to be used according to the methods of the invention in said MN/CA9 gene expression product detecting step (a) are nucleic acid-based assays, wherein said MN/CA9 gene expression product comprises a mRNA encoding an MN/CA IX protein or MN/CA IX polypeptide, or a cDNA complementary to mRNA encoding an MN/CA IX protein or MN/CA IX polypeptide. Preferably, said detecting step (a) is by PCR, RT-PCR, real-time PCR, or by quantitative real-time RT-PCR.

Preferably, the preneoplastic/neoplastic disease to be tested according to the prognostic methods of the invention for MN/CA9 gene expression product, is a disease which affects a tissue wherein 40% or more of the cells of said tissue, when unaffected by said preneoplastic/neoplastic disease, express MN/CA IX protein. Preferably said preneoplastic/neoplastic disease afflicting the subject vertebrate is selected from the group consisting of preneoplastic/neoplastic diseases of gastric mucosa, gallbladder, biliary ducts, ductal cells of duodenal glands, testis including ductular efferens and rete testis, ovary including surface coelomic epithelium and rete ovarii, basal cells of hair follicles, and central nervous systems choroid plexus. More preferably, said preneoplastic/neoplastic disease is selected from the group consisting of preneoplastic/neoplastic diseases of gastric mucosa, gallbladder, bilary ducts, and ductal cells of duodenal glands. Preferably said vertebrate is a mammal, more preferably human. Still more preferably, the vertebrate is a human patient, and said preneoplastic/neoplastic disease is selected from the group consisting of neoplastic diseases of gastric mucosa, gallbladder, biliary ducts and ductal cells of duodenal glands. Most preferably, said neoplastic disease is gastric cancer, and said sample is taken from the invasion front of said gastric cancer. Preferably, said neoplastic disease is a tumor, and said sample is taken from said tumor and/or from a metastatic lesion derived from said tumor.

Preferred prognostic methods according to the invention are those wherein a poorer prognosis is measured in terms of shortened survival, increased risk of recurrence of said preneoplastic/neoplastic disease, or in diminished or refractory response to treatment. Further preferred methods are those wherein said disease is neoplastic and comprises a tumor, or a tumor and one or more metastatic lesions derived from the tumor, and wherein a poorer prognosis is measured in terms of shortened survival, increased risk of recurrence of said neoplastic disease, or diminished or refractory response to treatment, following treatment and/or surgical removal of the tumor, or the tumor and said one or more metastatic lesions. Preferably, said prognostic method is used as an aid in the selection of treatment for said preneoplastic/neoplastic disease afflicting said vertebrate. Exemplary treatments include chemotherapy, radiation, and/or surgery.

In another aspect, this invention concerns methods which are prognostic for a preneoplastic/neoplastic disease afflicting a subject vertebrate, wherein said disease affects a tissue in which 40% or more of the cells normally express MN/CA IX protein, but said tissue loses or expresses MN/CA IX at a significantly reduced level upon carcinogenesis, comprising:

(a) taking a tissue sample from the invasion front of said preneoplastic/neoplastic disease;

(b) detecting in said invasion front sample whether MN/CA9 gene expression product is absent or at a significantly reduced level from the level that said MN/CA9 gene expression product is normally expressed in said tissue, when said tissue is unaffected by said disease; and (c) concluding that if said MN/CA9 gene expression product is neither absent nor at such a significantly reduced level in said invasion front sample, that the subject vertebrate has a poorer prognosis than if said MN/CA9 gene expression product were absent or at a such a significantly reduced level in said invasion front sample.

Aspects of the instant invention disclosed herein are described in more detail below.

REFERENCES

1. Parkkila and Parkkila, "Carbonic anhydrase in the alimentary tract. Roles of the different isozymes and salivary factors in the maintenance of optimal conditions in the gastrointestinal canal," *Scand J Gastroenterol.*, 31: 305-317 (1996).
2. Potter and Harris, "Diagnostic, prognostic and therapeutic implications of carbonic anhydrases in cancer," *Br J Cancer*, 89: 2-7 (2003).
3. Pastorek et al., "Cloning and characterization of MN, a human tumor-associated protein with a domain homologous to carbonc anhydrase and a putative helix-loop-helix DNA binding segment," *Oncogene*, 9: 2877-2888 (1994).
4. Opavsky et al. "Human MN/CA9 gene, a novel member of the carbonic anhydrase family: structure and exon to protein domain relationships," *Genomics*, 33: 480-487 (1996).
5. Zavada et al., "Expression of MaTu-MN protein in human tumor cultures and in clinical specimens," *Int J Cancer*, 54: 268-274 (1993).
6. Liao et al. "Identification of the MN antigen as a diagnostic biomarker of cervical intraepithelial neoplasia and cervical carcinoma," *Am J Pathol*, 145: 598-609 (1994).
7. Saarnio et al., "Immunohistochemical study of colorectal tumors for expression of a novel transmembrane carbonic anhydrase, MN/CA IX, with potential value as a marker of cell proliferation," *Am J Pathol*, 153: 279-285 (1998).
8. Svastova et al., "Carbonic anhydrase IX reduces E-cadherin-mediated adhesion of MDCK cells via interaction with β-catenin," *Exp Cell Res*, 290:332-345 (2003).
9. Wykoff et al. "Hypoxia-inducible expression of tumor-associated carbonic anhydrases," *Cancer Res*, 60: 7075-7083 (2000).
10. Koukourakis et al., "Hypoxia-regulated carbonic anhydrase-9 (CA9) relates to poor vascularization and resistance of squamous cell head and neck cancer to chemoradiotherapy," *Clin Cancer Res*, 7: 3399-3403 (2001).
11. Giatromanolaki et al. "Expression of hypoxia-inducible carbonic anhydrase-9 relates to angiogenic pathways and independently to poor outcome in non-small cell lung cancer," *Cancer Res.* 61:7992-7998 (2001).
12. Swinson et al., "Carbonic anhydrase IX expression, a novel surrogate marker of tumor hypoxia is associated with a poor prognosis in non-small cell lung cancer," *J Clin Oncol*, 21: 473-482 (2003).
13. Chia et al., "Prognostic significance of a novel hypoxia-regulated marker, carbonic anhydrase IX, in invasive breast carcinoma," *J Clin Oncol*, 19: 3660-3668 (2001).
14. Loncaster et al., "Carbonic anhydrase expression, a potential new intrinsic marker of hypoxia: correlations with tumor oxygen measurements and prognosis in locally advanced carcinoma of the cervix," *Cancer Res*, 61:6394-6399 (2001).
15. Pastorekova et al., "Carbonic Anhydrase IX: Analysis of stomach complementary DNA sequence and expression in human and rat alimentary tracts," *Gastroenterology*, 112: 398-408 (1997).
16. Leppilampi et al., "Carbonic anhydrase isozymes IX and XII in gastric tumors," *World J Gastroenterol*, 9: 1398-1403 (2003).
17. Gut et al., "Gastric hyperplasia in mice with targeted disruption of the carbonic anhydrase gene Car9," *Gastroenterology*, 123: 1889-1903 (2002).
18. Lauren P., "The two histological main types of gastric carcinoma: diffuse and so-called intestinal-type carcinoma," *Acta Path Microbiol Scand*, 64: 31-49 (1965).
19. Ebert et al., "Loss of beta-catenin expression in metastatic gastric cancer," *J Clin Oncol*, 21:1708-7114 (2003).
20. Juhasz et al., "Expression of carbonic anhydrase IX in human pancreatic cancer," *Aliment Pharmacol Ther*, 18: 837-846 (2003).
21. Krueger et al., "Cathepsin L antisense oligonucleotides in a human osteosarcoma cell line: Effects on the invasive phenotype," Cancer *Gene Therapy*, 8: 522-528 (2001).
22. Fuchs and Mayer, "Gastric carcinoma," *N Enql J Med*, 333: 32-41 (1995).
23. Ebert and Malfertheiner, "Pathogenesis of sporadic and familial gastric cancer: Implications for prevention and cancer management," *Alimentary Pharmacology Therapeutics*, 16:1059-1066 (2002).
24. Berx et al., "Mutations of the human E-cadherin (CDH1) gene," *Hum Mutat*, 12: 226-237 (1998).
25. Correa P, "Human gastric carcinogenesis: a multistep and multifactorial process—first American Cancer Society Award Lecture on cancer epidemiology and prevention" *Cancer Res*, 52: 6735-6740 (1992).
26. Stemmermann et al., "The molecular biology of esophageal and gastric cancer and their precursors: oncogenes, tumor suppressor genes, and growth factors," *Hum Pathol*, 25: 968-981 (1994).
27. Wingo et al., "The catalytic properties of human carbonic anhydrase IX," *Biochem Biophys Res Commun.* 288: 666-669 (2001).
28. Ivanov et al., "Down-regulation of transmembrane carbonic anhydrases in renal cell carcinoma cell lines by wild-type von Hippel-Lindau transgenes," *Proc Natl Acad Sci (USA)*, 95:12596-12601 (1998).
29. Maxwell et al., "The tumour suppressor protein VHL targets hypoxia-inducible factors for oxygen-dependent proteolysis," *Nature*, 399: 271-275 (1999).
30. Jaakkola et al. "Targeting of HIFα to the von Hippel Lindau ubiquitination complex by $O_2$-regulated prolyl hydroxylation," *Science*, 292:468-472 (2001).
31. Parkkila et al., "Carbonic anhydrase inhibitor suppresses invasion of renal cancer cells in vitro," *Proc Natl Acad Sci (USA)*, 97: 2220-2224 (2000).
32. Ashida et al., "Effects of von Hippel-Lindau gene mutation and methylation status on expression of transmembrane carbonic anhydrases in renal cell carcinoma," *J Cancer Res Clin Oncol*, 128: 561-568 (2002).
33. Cho et al., "Hypomethylation of the MN/CA9 promoter and upregulated MN/CA9 expression in human renal cell carcinoma," *Br J Cancer*, 85: 563-567 (2001).
34. Zhong et al., "Overexpression of hypoxia-inducible factor 1alpha in common human cancers and their metastases," *Cancer Res.* 59: 5830-5835 (1999).
35. Uemura et al., "Expression of Tumor-Associated Antigen MN/G250 in Urologic Carcinoma: Potential Therapeutic Target," *J. Urol.* 157 (4 Suppl.): 377 (Abstract 1475; 1997).
36. McKiernan et al., "Expression of the Tumor-associated Gene MN: A Potential Biomarker for Human Renal Cell Carcinoma," *Cancer Res.* 57: 2362-2365 (1997).
37. Stanbridge, E. J., "Cervical marker can help resolve ambiguous Pap smears," *Diagnostics Intelligence.* 10(5): 11 (1998).
38. Liao and Stanbridge, "Expression of the MN Antigen in Cervical Papanicolaou Smears Is an Early Diagnostic Biomarker of Cervical Dysplasia," *Cancer Epidemiology, Biomarkers & Prevention,* 5: 549-557 (1996);
39. Brewer et al., "A Study of Biomarkers in Cervical Carcinoma and Clinical Correlation of the Novel Biomarker MN," *Gynecologic Oncology* 63: 337-344 (1996).
40. Uemura et al., "MN/CA IX/G250 as a potential target for immunotherapy of renal call carcinomas," *Br. J. Cancer,* 81:741-746 (1999).
41. Bretheau et al., "Prognostic value of nuclear grade of renal cell carcinoma," *Cancer,* 76:2543-2549 (1995).
42. Bui et al., "Carbonic Anhydrase IX Is an Independent Predictor of Survival in Advanced Renal Clear Cell Carcinoma: Implications for Prognosis and Therapy," *Clin. Cancer Res.,* 9: 802-811 (2003).
43. Risio, M., "Cell proliferation in colorectal tumor progression: an immunohistochemical approach to intermediate biomarkers," *J. Cell Biochem,* 16G: 79-87 (1992).
44. Moss et al., "Inward growth of colonic adenomatous polyps," *Gastroenterology,* 111: 1425-1432 (1996).
45. Pastorekova and Zavada, "Carbonic anhydrase IX (CA IX) as a potential target for cancer therapy," *Cancer Therapy,* 2: 245-262 (2004).
46. Glennie et al., "Univalent antibodies kill tumour cells in vitro and in vivo," *Nature,* 295: 712 (1982).
47. Dalbadie-MacFarland et al., "Oligonucleotide-directed mutagenesis as a general and powerful method for studies of protein function," *PNAS USA* 79: 6409 (1982).
48. Hunter, W. M., "Radioimmunoassay," In: *Handbook of Experimental Immunology* pp. 14.1-14.40 (D. W. Weir ed.; Blackwell, Oxford/London/Edinburgh/Melbourne; 1978).
49. Ivanov et al., "Expression of hypoxia-inducible cell-surface transmembrane carbonic anhydrases in human cancer." *Am J Pathol,* 158 (3): 905-919 (2001).
50. Kivela et al., "Expression of transmembrane carbonic anhydrase isozymes IX and XII in normal human pancreas and pancreatic tumours," *Histochem Cell Biol,* 114: 197-204 (2000).
51. Karhumaa et al., "Expression of the transmembrane carbonic anhydrases, CA IX and CA XII, in the human male excurrent ducts," *Mol Hum Reprod,* 7: 611-616 (2001).
52. Turner et al., "MN antigen expression in normal, preneoplastic, and neoplastic esophagus: A clinicopathological study of a new cancer-associated biomarker," *Human Pathol,* 28: 740-744 (1997).
53. Liao et al., "Identification of the MN/CA9 protein as a reliable diagnostic biomarker of clear cell carcinoma of the kidney," *Cancer Res.* 57: 2827-2831 (1997).
54. Saarnio et al., "Transmembrane carbonic anhydrase, MN/CA IX, is a potential biomarker for biliary tumors," *J Hepatol,* 35: 643-649 (2001).
55. Leff, D. N., "Half a Century of HeLa Cells: Transatlantic Antigen Enhances Reliability of Cervical Cancer Pap Test, Clinical Trials Pending," *BioWorld. RTM, Today: The Daily Biotechnology Newspaper,* 9(55) (Mar. 24, 1998).
56. Pastorekova et al. "A novel quasi-viral agent, MaTu, is a two component system," *Virology,* 187:620-626 (1992)

ABBREVIATIONS

The following abbreviations are used herein:

| | |
|---|---|
| aa | amino acid |
| ATCC | American Type Culture Collection |
| AZA | azadeoxycytidine |
| bp | base pairs |

-continued

| | |
|---|---|
| BRL | Bethesda Research Laboratories |
| CA | carbonic anhydrase |
| ° C. | degrees centigrade |
| CDR | complementarity determining region |
| DMEM | Dulbecco modified Eagle medium |
| DMSO | dimethyl sulfoxide |
| ds | double-stranded |
| DTT | dithiothreitol |
| EDTA | ethylenediaminetetraacetate |
| FCS | fetal calf serum |
| FITC | fluorescein isothiocyanate |
| HRP | horseradish peroxidase |
| IC | intracellular |
| IRS | immunoreactivity score |
| kb | kilobase |
| kbp | kilobase pairs |
| kd or kDa | kilodaltons |
| LTR | long terminal repeat |
| M | molar |
| MAb | monoclonal antibody |
| ME | mercaptoethanol |
| min. | minute(s) |
| mg | milligram |
| ml | milliliter |
| mM | millimolar |
| MMLV | Moloney murine leukemia virus |
| mmol | millimole |
| N | non-neoplastic gastric mucosa |
| ng | nanogram |
| nm | nanometer |
| nM | nanomolar |
| nt | nucleotide |
| ORF | open reading frame |
| PCR | polymerase chain reaction |
| PG | proteoglycan |
| pl | isoelectric point |
| pmol | picamolar |
| RCC | renal cell carcinoma |
| RNP | RNase protection assay |
| RT-PCR | reverse transcription polymerase chain reaction |
| SDS | sodium dodecyl sulfate |
| SP | signal peptide |
| SSP | standard saline phosphate ethylenediaminetetraacetic acid |
| T | gastric tumor |
| TM | transmembrane |
| Tris | tris (hydroxymethyl) aminomethane |
| U | units |
| µg | microgram |
| µl | microliter |
| µM | micromolar |

CELL LINES

AGS—human gastric cancer cell line; gastric adenocarcinoma [American Type Culture Collection (ATCC), Rockville, Md.]

HeLa cells—human cervical cancer cell line; epithelial adenocarcinoma [American Type Culture Collection (ATCC), Rockville, Md.]

MKN45—human gastric cancer cell line; poorly differentiated adenocarcinoma [Riken Cell Bank, Tsukuba, Japan]

MKN28—human gastric cancer cell line; moderately differentiated tubular adenocarcinoma [Riken Cell Bank, Tsukuba, Japan]

N87—human gastric cancer cell line; gastric carcinoma derived in 1976 by A. Gazdar from liver metastatic site [American Type Culture Collection (ATCC), Rockville, Md.]

NUCLEOTIDE AND AMINO ACID SEQUENCE SYMBOLS

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIG. 1A-C provides the nucleotide sequence for MN/CA IX full-length cDNA [SEQ ID NO: 1]. FIG. 1 A-C also sets forth the predicted amino acid sequence encoded by the cDNA [SEQ ID NO: 2.].

FIG. 2A-F provides a 10,898 bp complete genomic sequence of MN/CA9 [SEQ ID NO: 3]. The base count is as follows: 2654 A; 2739 C; 2645 G; and 2859 T. The 11 exons are in general shown in capital letters, but exon 1 is considered to begin at position 3507 as determined by RNase protection assay.

FIG. 3 provides an exon-intron map of the human MN/CA9 gene. The positions and sizes of the exons (numbered, cross-hatched boxes), Alu repeat elements (open boxes) and an LTR-related sequence (first unnumbered stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail). Below the map, the alignment of amino acid sequences illustrates the extent of homology between the MN/CA IX protein PG region (aa 53-111) [SEQ ID NO: 4] and the human aggrecan (aa 781-839) [SEQ ID NO: 5].

FIG. 4 (discussed in Example 2) shows results from Western blot analysis and real-time PCR of CA IX protein and CA9 mRNA in gastric cancer. (A) Western blot analysis revealed reduced CA IX protein levels in gastric cancer (T) compared with the non-neoplastic gastric mucosa (N). CA IX was identified as a protein with 54 and 58 kDa. β-actin protein levels were assessed for standardization of protein levels. No CA IX protein was detected in AGS cells, whereas low levels were found in N87 and MKN28 cells. Hela cells served as a control. (B) Quantitative analysis of CA9 mRNA and CA IX protein levels in gastric tumors (T) as assessed by Western blot analysis and real-time PCR compared to the matched non-neoplastic gastric mucosa (N). In 5 cases protein and mRNA levels were assessed in both the cancerous and non-cancerous tissues and exhibited decreased levels in the cancerous part in all cases.

FIG. 5 (discussed in Example 3) provides survival analysis of patients with gastric cancer expressing low or high levels of the CA IX protein. Using an immunoreactivity score as outlined in *Materials and Methods*, a group of patients with a IRS≦3 (CA IX−) and a second group with a IRS >3 (CA IX+) were identified. Survival was significantly shorter in patients with increased CA IX expression (score) >3; CA IX+) (p=0.0281).

FIG. 6 (discussed in Example 4) provides in vitro analysis of CA IX overexpression in AGS gastric cancer cells. (A) Cellular invasion of AGS cells transfected with CA9 cDNA (CA9), incubated with the Transfectam reagent without DNA (control A) or transfected with the empty pCMVβ vector (control B) was evaluated in 24-well Transwell chambers (Costar, Bodenheim, Germany) as described above. The differences between AGS cells transfected with the empty pCMVβ vector and the CA9 transfected cells, as well as the cells without DNA transfer and the CA9 transfected cells were statistically significant (two-tailed, unpaired t test; mean±SD). Bars, mean±SD. (B) Induction of cell proliferation by CA9 transfection in AGS cancer cells. Transfection of AGS cells with CA9 cDNA led to a significant induction of cell proliferation compared to cells without DNA transfection (control A) or transfected with an empty PCMVβ vector (control B) (two-tailed, unpaired t test; mean±SD). Bars, mean±SD.

FIG. 7 (discussed in Example 5) shows analysis of methylation effects on CA IX expression in gastric cancer cell lines. (A) CA9 mRNA levels in gastric cancer cell lines were assessed with and without incubation with 5'-azadeoxycytidine (AZA). Basal mRNA expression (white columns) was standardized in all cells and the relative changes after incubation with 5'-azadeoxycytidine (grey columns) was assessed by realtime PCR. While no significant change was observed for MKN28 cells, the other cells, i.e. AGS, MKN45 and N87 cells, exhibited a more than 5-fold increase in CA9 mRNA levels following treatment with 5'-azadeoxycytidine (AZA). (B) Cellular invasion of AGS cells treated with or without DMSO or 5'-azadeoxycytidine was evaluated in 24-well Transwell (8 µm pore size) chambers (Costar, Bodenheim, Germany). Invading cells were harvested from the lower side of the filters by using trypsin/EDTA. Cell number was quantified in a Coulter Counter ZII (Coulter Immunotech, Marseille, France). The differences between 5'-azadeoxycytidine (AZA) and untreated AGS cells (AGS, DMSO) was statistically significant (two-tailed, unpaired t test; mean±SD). Bars, mean±SD.

DETAILED DESCRIPTION

The novel methods of the present invention demonstrate that the gene expression products of the cancer-related CA9 gene are associated with survival of a vertebrate afflicted with a preneoplastic/neoplastic disease, wherein said disease affects a tissue which normally expresses MN/CA IX protein, but loses or has significantly reduced CA IX expression upon carcinogenesis. Exemplary of such preneoplastic/neoplastic diseases are preneoplastic/neoplastic diseases of gastric mucosa, gallbladder, biliary ducts, ductal cells of duodenal glands, testis including ductular efferens and rete testis, ovary including surface coelomic epithelium and rete ovarii, basal cells of hair follicles, or central nervous system choroid plexus. In particular, the levels of CA9 gene expression products can be used to predict clinical outcome and to identify high risk patients in need of adjuvant therapies.

The invention provides methods for prognosis of diseases associated with tissues that normally express CA IX protein, preferably a preneoplastic/neoplastic disease of gastric mucosa, gallbladder, biliary ducts, and ductal cells of duodenal glands. The methods include quantifying MN/CA9 gene expression product, if any, present in a sample taken from a patient diagnosed with such a preneoplastic/neoplastic disease; the MN/CA9 gene expression product can be CA IX protein, CA IX polypeptide, mRNA encoding a CA IX protein or polypeptide, a cDNA corresponding to an mRNA encoding a CA IX protein or polypeptide, or the like. The quantified MN/CA9 gene expression product levels are compared with the average levels in comparable samples taken from comparable patients, and correlated with a better or worse prognosis for the patient. Said CA9 gene expression product is preferably a CA IX protein or CA IX polypeptide quantitated in a sample taken from the patient.

The use of gene expression products of oncogenes as prognostic indicators for preneoplastic/neoplastic diseases is considered conventional by those of skill in the art. However, the application of such approaches to a preneoplastic/neoplastic disease, wherein said disease affects a tissue which normally expresses CA IX protein, but has significantly reduced CA IX expression upon carcinogenesis, is new. In contrast to the methods of prognosis for many other CA IX-associated preneoplastic/neoplastic diseases that are not the subject of the present invention, which affect tissues which normally do not express CA IX protein, (i.e., most tissue types), the methods of the present invention indicate a poorer prognosis when CA IX gene expression product is expressed at a higher level than average when compared to CA9 gene expression product levels in comparable affected tissues.

Preneoplastic/neoplastic Tissues

Preferably, said preneoplastic/neoplastic tissue is one in which 40% or more of the cells of said tissue express CA IX protein, when unaffected by preneoplastic/neoplastic disease. Exemplary normal human tissues expressing CA IX protein at such a level, as identified, for example, by immunohistochemical staining using the monoclonal antibody M75 and exemplary matched neoplastic tissues, have previously been described in detail [45, 49]. In the gastrointestinal tract, diffuse CA IX immunoreactivity has been observed in the gastric mucosa, ductal cells of duodenal glands, and crypt cells of the duodenum, jejunum, and to a lesser degree, in the terminal ileum and appendix. High levels of CA IX expression have been consistently observed in the basal cells in and near the infundibulum and medulla of the hair follicle, mesothelial cells, and coelomic epithelium of the body cavities. In the visceral organs, high levels of CA IX expression in the epithelium have been identified but limited to rete ovarii, rete testis, ductular efferens, bile ducts, and gallbladder. In the peripheral and central nervous systems, CA IX expression is limited to the ventricular lining cells and the choroid plexus.

According to the methods of the invention, the preneoplastic/neoplastic tissue that is the subject of the invention is one that not only normally expresses CA IX protein, but also loses or has significantly reduced CA IX protein expression upon carcinogenesis, such as stomach and gallbladder tissues [16, 45, 54].

As used herein, "cancerous" and "neoplastic" have equivalent meanings, and "precancerous" and "preneoplastic" have equivalent meanings.

Intestinal metaplasia is defined to be "the transformation of mucosa, particularly in the stomach, into glandular mucosa resembling that of intestines, although usually lacking villi." [Stedman's Medical Dictionary, 26$^{th}$ Edition (Williams & Wilkins; Baltimore, Md., USA; 1995).].

The large intestine is defined as "the portion of the digestive tube extending from the ileocecal valve to the anus; it comprises the cecum, colon, rectum, and anal canal. SYN intestinum crassum." [Id.]

The colon is "[t]he division of the large intestine extending from the cecum to the rectum." [Id.]

Duodenal glands are "small, branched, coiled tubular glands that occur mostly in the submucosa of the first third of the duodenum; they secrete an alkaline mucoid substance that serves to neutralize gastric juice. SYN glandulae duodenales . . . , Brunner's g.'s, Wepfer's g.'s." [Id.]

In a preferred embodiment of the invention, the MN/CA9 gene expression product is CA IX antigen, and the CA IX antigen is quantitated in preneoplastic/neoplastic vertebrate samples, preferably mammalian samples, more preferably human samples. Such preneoplastic/neoplastic samples can be tissue specimens, tissue extracts, cells, cell lysates and cell extracts, among other samples. Preferred tissue samples are formalin-fixed, paraffin-embedded tissue samples or frozen tissue samples. In a preferred embodiment, the disease is gastric cancer, and the sample is taken from the invasion front of the gastric cancer.

It can be appreciated by those of skill in the art that various other preneoplastic/neoplastic samples can be used to quantify the CA IX gene expression products. For example, in the case of a patient afflicted with a neoplastic disease, wherein the disease is a tumor, the sample may be taken from the tumor or from a metastatic lesion derived from the tumor.

It can further be appreciated that alternate methods, in addition to those disclosed herein, can be used to quantify the CA9 gene expression products. In preferred embodiments, the gene expression product is CA IX antigen which is detected and quantified by immunohistochemical staining (e.g., using tissue arrays or the like). Preferred tissue specimens to assay by immunohistochemical staining, for example, include cell smears, histological sections from biopsied tissues or organs, and imprint preparations among other tissue samples. An exemplary immunohistochemical staining protocol is described below in the *Materials and Methods* section. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

Assays

Assays using MN proteins/polypeptides and/or MN nucleic acids, as the methods described herein, may be both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease.

The screening methods of the instant invention are useful for screening a variety of preneoplastic/neoplastic diseases as indicated herein. It can be envisioned that at the same time that a disease, which is the subject of the prognostic methods of the instant invention, is first diagnosed, as for example, gastric cancer, that the level of MN gene expression product could also provide prognostic information. For example, a gastric cancer could be simultaneously diagnosed and prognosed; reduced or absent MN gene expression product in the bulk of a gastric tissue sample would be diagnostic, whereas the presence of significant MN gene expression product at the invasion front would be prognostic. The normal level of MN expression in non-neoplastic epithelium adjacent to such a gastric cancer would be maintained.

The assays of this invention can also be used to confirm the absence or removal of all tumor tissue following surgery, cancer chemotherapy and/or radiation therapy. It can further be used to monitor cancer chemotherapy and tumor reappearance.

Many formats can be adapted for use with the methods of the present invention. The detection and quantitation of CA IX protein or CA9 polypeptide can be performed, for example, by Western blots, enzyme-linked immunosorbent assays, radioimmunoassays, competition immunoassays, dual antibody sandwich assays, immunohistochemical staining assays, agglutination assays, fluorescent immunoassays, cytofluorometry, immunoelectron and scanning microscopy using immunogold, among other assays commonly known in the art. The quantitation of CA9 gene expression products in such assays can be adapted by conventional methods known in the art; for example, if the detection method is by immunohistochemical staining, the quantitation of CA IX protein or CA IX polypeptide can be performed by determining the percentage of immunoreactive cells and/or the intensity of immunostaining of immunoreactive cells, and can additionally comprise addition or multiplication of these values, or other mathematical calculations using these values.

It is also apparent to one skilled in the art of immunoassays that CA IX proteins or polypeptides can be used to detect and quantitate CA IX antigen in body tissues and/or cells of patients. In one such embodiment, an immunometric assay may be used in which a labelled antibody made to CA IX protein is used. In such an assay, the amount of labelled antibody which complexes with the antigen-bound antibody is directly proportional to the amount of CA IX antigen in the sample.

Exemplary Immunohistochemical Assays

The distribution and expression pattern of MN/CA IX was investigated by immunohistochemistry, described in Example 1. Tissue sections were stained with the MN/CA IX-specific monoclonal antibody M75. Exemplary immunohistochemical staining results show MN/CA IX in the non-neoplastic gastric mucosa, intestinal metaplasia and significantly less often in gastric cancer. A lack of MN/CA IX immunostaining was found in gastric cancer of a moderately (G2) differentiated intestinal type and in a diffuse type of gastric cancer, whereas the neighboring non-neoplastic epithelial cells showed strong immunostaining. Occasionally the immunostaining was found to be heterogeneous. For example, a poorly differentiated (G3) intestinal type gastric cancer was found with no immunostaining of the tumor cells in the gastric mucosa, but with intense staining in a subset of the tumor cells infiltrating the muscularis propria.

Immunohistochemical analysis, described in Example 3, revealed a further important observation. After applying an immunoreactivity score, two groups of CA IX expression patterns were identified in gastric cancer. Cancers expressing abundant CA IX exhibited a shorter post-operative survival compared to tumors with low levels of CA IX expression or no expression at all. A similar association of CA IX expression and poor prognosis has recently also been reported in non-small-cell lung cancers [12]; however, unlike gastric cancer normal lung tissue does not express CA IX at appreciable levels. In the further analysis of the immunohistochemical sections of gastric cancers that retained CA IX expression, CA IX expression was observed primarily in cancer cells that were located at the invasion front, indicating that while a loss of CA IX expression is a frequent event in gastric cancer, those gastric tumors that retain CA IX expression exhibit increased invasiveness, which could contribute to their poor prognosis [31]. In vivo observations made in arriving at the instant invention are supported by the in vitro analysis of CA IX overexpression in AGS gastric cancer cells, described in Example 4. Upon transfection of CA9 cDNA in such gastric cancer cells, the cell proliferation and invasive growth of the transfected cells was significantly enhanced. Thus, overexpression of CA IX in gastric cancer is also associated with enhanced cell proliferation and invasion, strengthening the finding of CA IX expression at the invasion front of gastric cancers, which also exhibit a worse prognosis.

While overexpression of CA IX has been reported in various cancers, the expression is low or even lost in most gastric cancers [15,16]. An analysis by inventors of the subject prognostic methods showed that CA IX expression was lost in the cancer cells in 26 of 57 patients, whereas in the normal stomach expression of CA IX was retained in foveolar epithelial cells and in fundic and antral glands. A previous study by Pastorekova et al. assessed the expression of CA IX in a limited number of specimens and also reported decreased CA IX expression in the gastric cancers that were studied [15]. While the loss of expression of CA IX could be interpreted as a consequence of the neoplastic changes, including dedifferentiation during gastric carcinogenesis, recent studies indicate that in fact this loss is not just an epiphenomenon but instead a critical change underlying the process of gastric carcinogenesis. That hypothesis is supported by the generation of CA IX deficient mice, in which the inactivation of the CA IX gene led to the development of gastric hyperplasia, which is associated with enhanced cellular proliferation [17]. Together with the study of inventors of the subject prognostic methods that demonstrated loss of CA IX expression in approximately half of the gastric cancers, those studies in CA IX deficient mice indicate that CA IX may function as a critical differentiation factor in the stomach that also controls cell proliferation and growth of the gastric mucosa. Indeed, the loss of CA IX expression as disclosed herein in the Western blot and PCR analyses may support the hypothesis that such a loss of CA IX expression is critical for the development of gastric cancer and may be an early event in gastric carcinogenesis.

Nucleic Acid-Based Assays

In certain embodiments of the invention, mRNA that encodes a CA IX protein or a CA IX polypeptide or the cDNA complementary to that mRNA is detected and quantitated in a sample taken from a patient afflicted with a preneoplastic/neoplastic disease, such as gastric cancer, compared with the average of MN/CA9 mRNA levels in comparable samples, and thereby correlated with a prognosis for a patient. Where expression of MN/CA9 mRNA or MN/CA9 cDNA is measured, above average CA9 mRNA or above average CA9 cDNA expression is indicative of a poorer prognosis. One preferred method for measuring alterations in the level of CA9-specific mRNA expression is Northern blotting, where the nucleic acid sequence used as a probe for detecting MN/CA9-specific mRNA expression is complementary to all or part of the MN/CA9 cDNA sequence shown in FIG. 1; a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography. The samples may be stained with hematoxylin to demonstrate the histological composition of the sample, and dark field imaging with a suitable light filter illuminates the developed emulsion. Non-radioactive labels such as digoxigenin may also be used.

A second preferred method for measuring CA9-specific mRNA expression is detection of CA9 mRNA expression via hybridization of a nucleic acid probe derived from MN/CA9 cDNA sequence to RT-PCR products generated from RNA isolated from a biological sample.

Exemplary Western Blot and PCR Assays

Additionally, methods can be used in combination; for example, CA9 mRNA and CA IX protein expression can be assessed by realtime quantitative PCR and/or by Western blotting, such as in tumor samples from patients with gastric cancer and matched samples of corresponding non-neoplastic gastric mucosa. As described in Example 2, in all five cases in which both Western blot analysis and realtime quantitative PCR were performed in the same patient, CA IX protein levels were significantly decreased in gastric cancers compared to the matched non-neoplastic mucosa, and were associated with decreased CA9 mRNA levels (FIG. 4).

MN Gene and Protein

The terms "MN/CA IX" and "MN/CA9" are herein considered to be synonyms for MN. Also, the G250 antigen is considered to refer to MN protein/polypeptide [35].

Zavada et al., WO 93/18152 and/or WO 95/34650 disclose the MN cDNA sequence shown herein in FIGS. 1A-1C [SEQ ID NO: 1], the MN amino acid sequence [SEQ ID NO: 2] also shown in FIGS. 1A-1C, and the MN genomic sequence [SEQ ID NO: 3] shown herein in FIGS. 2A-2F. The MN gene is organized into 11 exons and 10 introns.

The ORF of the MN cDNA shown in FIG. 1 has the coding capacity for a 459 amino acid protein with a calculated molecular weight of 49.7 kd. The overall amino acid composition of the MN/CA IX protein is rather acidic, and predicted to have a pI of 4.3. Analysis of native MN/CA IX protein from CGL3 cells by two-dimensional electrophoresis followed by immunoblotting has shown that in agreement with computer prediction, the MN/CA IX is an acidic protein existing in several isoelectric forms with pIs ranging from 4.7 to 6.3.

The first thirty seven amino acids of the MN protein shown in FIGS. 1A-1C is the putative MN signal peptide [SEQ ID NO: 6]. The MN protein has an extracellular domain [amino acids (aa) 38-414 of FIGS. 1A-1C [SEQ ID NO: 7], a transmembrane domain [aa 415-434; SEQ ID NO: 8] and an intracellular domain [aa 435-459; SEQ ID NO: 9]. The extracellular domain contains the proteoglycan-like domain [aa 53-111: SEQ ID NO: 4] and the carbonic anhydrase (CA) domain [aa 135-391; SEQ ID NO: 5].

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

MN Proteins and Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies, preferably the Mab M75 or its equivalent. The VU-M75 hybridoma that secretes the M75 Mab was deposited at the ATCC under HB 11128 on Sep. 17, 1992.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

Nucleic Acid Probes

Nucleic acid probes of this invention are those comprising sequences that are complementary or substantially complementary to the MN cDNA sequence shown in FIG. 1 or to other MN gene sequences, such as, the complete genomic sequence of FIGS. 2A-F [SEQ ID NO: 3]. The phrase "substantially complementary" is defined herein to have the meaning as it is well understood in the art and, thus, used in the context of standard hybridization conditions. The stringency of hybridization conditions can be adjusted to control the precision of complementarity. Two nucleic acids are, for example, substantially complementary to each other, if they hybridize to each other under stringent hybridization conditions.

Stringent Hybridization Conditions

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. such as, 0.15 M to 0.9 M salt at temperatures ranging from 20° C. to 55° C. Less stringent conditions can be made more stringent by adding increasing amounts of formamide, which serves to destabilize hybrid duplexes as does increased temperature, such as provided by exemplary stringent hybridization conditions, such as, 0.15 M to 0.9 M NaCl in the presence of 50% formamide at 42° C. with a final wash of 0.1% SSPE and 0.1% SDS at 65° C.

Further exemplary stringent hybridization conditions are described in Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982); Tsuchiya et al., *Oral Surgery, Oral Medicine, Oral Pathology*. 71(6): 721-725 (June 1991); and in U.S. Pat. Nos. 5,989,838, 5,972,353, 5,981,711, and 6,051,226.

Only very closely related nt sequences having a homology of at least 80-90% would hybridize to each other under stringent conditions.

Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen. Humanized and fully human antibodies fall with the definition of "antibodies" herein.

Antibodies useful according to the methods of the invention may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies [46]; Fab proteins including Fab' and F(ab)$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of the $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also oligonucleotide-directed mutagenesis techniques [47].

The antibodies useful according to this invention to identify CA IX proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [48].

Representative monoclonal antibodies useful according to this invention include Mabs M75, MN9, MN12, MN7 and V/10 described in earlier Zavada et al. patents and patent applications. [U.S. Pat. Nos. 6,297,041; 6,204,370; 6,093,548; 6,051,226; 6,004,535; 5,989,838; 5,981,711; 5,972,353; 5,955,075; 5,387,676; US Application Nos: 20030049828 and 20020137910; and International Publication No. WO 03/100029]. Monoclonal antibodies useful according to this invention serve to identify MN proteins/polypeptides in various laboratory prognostic tests, for example, in clinical samples. For example, monoclonal antibody M75 (Mab M75) is produced by mouse lymphocytic hybridoma VU-M75, which was deposited under ATCC designation HB 11128 on Sep. 17, 1992 at the American Tissue Type Culture Collection [ATCC]. The production of hybridoma VU-M75 is described in Zavada et al., International Publication No. WO 93/18152. Mab M75 recognizes both the nonglycosylated GST-MN fusion protein and native CA IX protein as expressed in CGL3 cells equally well. The M75 Mab recognizes both native and denatured forms of the CA IX protein [56].

General texts describing additional molecular biological techniques useful herein, including the preparation of antibodies include Berger and Kimmel, *Guide to Molecular Cloning Techniques, Methods in Enzymology*, Vol. 152, Academic Press, Inc., Sambrook et al., *Molecular Cloning: A Laboratory Manual*, (Second Edition, Cold Spring Harbor Laboratory Press; Cold Spring Harbor, N.Y.; 1989) Vol. 1-3; *Current Protocols in Molecular Biology*, F. M. Ausabel et al. [Eds.], Current Protocols, a joint venture between Green Publishing Associates, Inc. and John Wiley & Sons, Inc. (supplemented through 2000), Harlow et al., *Monoclonal Antibodies: A Laboratory Manual*, Cold Spring Harbor Laboratory Press (1988), Paul [Ed.]; *Fundamental Immunology*, Lippincoft Williams & Wilkins (1998), and Harlow et al., *Using Antibodies: A Laboratory Manual*, Cold Spring Harbor Laboratory Press (1998).

MATERIALS AND METHODS

Subjects. Tumorous and corresponding non-tumorous paraffin embedded tissue specimens from 59 patients (20 female, 39 male, age range 41-84 years) were retrieved from the archive of the Institute of Pathology of the University of Magdeburg for immunohistochemical analyses. 27 patients had suffered from diffuse type and 32 from intestinal type gastric cancer, according to the Lauren classification [18]. For molecular analyses gastric cancer and corresponding non-lesional tissue were obtained immediately after surgery from 18 patients with gastric cancer (2 female, 16 male, age range 43-82 years). Tissue samples were snap-frozen in liquid nitrogen and stored at −80° C. and further processed as described below, or fixed in 10% neutralized formalin and embedded in paraffin for histological processing. The study was approved by the Human Subjects Committee of the University of Magdeburg, Germany.

Cell lines. The gastric cancer cell lines MKN45, MKN28, AGS, N87 and the Hela cells were obtained from Riken Cell Bank (Tsukuba, Japan) and the American Type Culture Collection (ATCC, Rockville, Md.). All cell lines, except AGS and Hela cells, were maintained in RPMI medium (Gibco BRL, Rockville, Md., USA) with 10% fetal bovine serum. The AGS cell line was kept in F-12K medium with 10% fetal bovine serum and the Hela cells were cultured in Dulbecco's modified Eagle medium (DMEM, Gibco BRL, Rockville, Md., USA) supplemented with 10% fetal bovine serum.

Transient transfection assay. AGS gastric cancer cells were seeded at a density of $2 \times 10^5$ cells/60 mm dish. The cells were transfected 24 hrs later with a pSG5C vector (5 µg) containing the human CA9 cDNA (1.5 kb, Kpnl/Sacl site)[3], or an empty pCMVβ vector (control B) or were incubated with the Transfectam reagent alone (control A) (Promega, Mannheim) according to the manufacturer's recommendations with the optimal volume/weight ratio of Transfectam Reagent/DNA of 2 µl/µg DNA. Protein expression was confirmed after 24 hrs, 48 hrs and 72 hrs by Western blot analysis (not shown).

Treatment of cells with 5-aza-dC. Cells were seeded at a density of $1 \times 10^6$ cells/60 mm dish. Twenty-four hours later, the cells were treated with 5 µM 5-aza-dC (Sigma Chemical Co., Deisenhofen, Germany). The same concentration of DMSO was also used as a control for nonspecific solvent effect on cells. Total cellular protein was isolated 3 days after addition of 5-aza-dC as previously described [19].

Cell proliferation assay. AGS cells were grown in media supplemented with 10% fetal calf serum (Gibco Invitrogen) and 50 µg/ml rifobacin. Parental AGS cells, AGS cells transfected with the pCMVβ vector and CA IX transfected AGS cells were seeded in 96 well plates at a density of $30 \times 10^4$ cells/200 µl/well. After 40 hrs of culture at 37° C., 5% (v/v) $CO_2$, cells were pulsed for an additional 8 hrs with $_3$H-methyl-thymidine (0.2 µCi/well), and harvested onto glass fibre membranes. The incorporated radioactivity was measured by scintillation counting. In each case DNA synthesis was assessed 6 times in parallel and repeated once, resulting in a total of 12 experiments per cell line [20].

In vitro invasion assay. Cellular invasion of AGS cells was evaluated in 24-well Transwell chambers (Costar, Bodenheim, Germany) as described previously [21]. The upper and lower culture compartments were separated by polycarbonate filters with 8 µm pore size. Prior to invasion assays, the polycarbonate filter was coated with 100 ng matrigel matrix. For invasion assays, $3 \times 10^4$ cells per well were incubated on the reconstituted basement membrane for 72 hrs. Cells passing the filters and attaching to the lower sites of matrigel-coated membranes were harvested using trypsin/EDTA; the cell number was quantified in a Coulter Counter ZII (Coulter Immunotech, Marseille, France). The number of migrating cells was calculated from controls grown under identical culture conditions for 72 hrs in 24 well plates. All experiments were performed in triplicate.

Real-time quantitative analysis of CA9 mRNA levels. Tissue specimens were homogenized with an ultrasound homogenizer (Ultra-Turrax T25 basic, IKA, Staufen, Germany). Total RNA (1 µg) was reverse transcribed at 37° C. for 1 hr in a final volume of 20 µl reverse transcription buffer (50 mM Tris-HCl pH 8.3, 7 mM $MgCl_2$ and 40 mM KCl and 10 mM DTT) containing 100 U MMLV reverse transcriptase, Rnase H Minus, Point Mutant (Promega, Mannheim, Germany), 16 U RNase inhibitors (Promega), 200 p mol random primer (Promega) and 0.5 mM dNTPs (Biomol Feinchemikalien, Hamburg, Germany). Briefly, PCR primers were designed to amplify a 240 bp cDNA fragment of the CA IX gene (sense 5'-AGGAGGATCTGCCCAGTGA-3' [SEQ ID NO: 10]; antisense 5'-GCCMTGACTCTGGTCATC-3') [SEQ ID NO: 11][4]. The expression level of CA IX was determined by using the LightCycler technique (Roche Diagnostics GmbH, Mannheim, Germany) as previously described [20].

Immunohistochemistry. Deparaffinized serial sections were cut at 3 µm for immunohistochemistry and placed on Superfrost Plus glass slides. Immunostaining was performed with a monoclonal antibody M75 directed against CA IX [15]. For immunostaining, sections were deparaffinized in xylene and rehydrated in an alcohol series. Anti-CA IX (dilution 1:10) was administered for 1 hr at 37° C. in a moist chamber, followed by incubation with biotinylated anti-mouse IgG/anti-rabbit IgG (1:200; Vector Laboratories; distributed by Camon, Wiesbaden, Germany) and ABC alkaline phosphatase reagent, each for 30 min at room temperature. Between steps the sections were washed in Tris buffered saline. Immunoreactions were visualized with the avidin biotin complex method applying a Vectastain ABC alkaline phosphatase kit (distributed by Camon, Wiesbaden, Germany). Neufuchsin served as chromogen. All specimens were counterstained with hematoxylin. Primary antibodies were omitted for negative controls.

Evaluation of immunohistochemical results. A numerical scoring system with two categories was used to assess the observed expression of CA IX in tumor cells and gastric epithelium. Category A documented the number of immunoreactive cells as 0 (no immunoreactive cells), 1 (<10%), 2 (11 to 50%), and 3 (>50%). A positive case was defined as having a Category A value of 1. Category B documented the intensity of the immunostaining as 0 (no immunostaining), 1 (weak), 2 (moderate), and 3 (strong). Finally, the values for Category A and B were added to give the "immunoreactivity score" (IRS), which could range from 0 to 6. Note that the method of calculating the IRS does not allow the individual categories to add up to an IRS of 1.

Western blot analysis. Human gastric tissues and cell lines were lysed in a buffer containing 1 mM EDTA, 50 mM β-glycerophosphate, 2 mM sodium orthovanadate, 1% Triton-100, 10% glycerol, 1 mM DTT and protease inhibitors (10 mg/ml benzamidine, 2 mg/ml antipain, and 1 mg/ml leupeptin). After separation, proteins were electroblotted onto polyvinylidene difluoride membranes (Bio-Rad). The membrane was incubated with 1:200 anti-CA IX M75 antibody for 1 hr at room temperature, as previously described [20]. Membrane-bound secondary antibodies were detected by enhanced chemiluminescence following the instructions of the manufacturer. To ensure equal loading amounts, the blots were stripped in 200 mmol/L glycine, 1% Tween-20, 0.1% SDS, pH 2.2, for 2 hrs at room temperature and rehybridized using a monoclonal anti-α-actin antibody (dilution 1:2000; clone AC-74; Sigma) [19].

Statistical analysis. The number of proliferating/invading cells and the expression of CA IX was analysed using student's t test. The survival curve was plotted using the Kaplan-Meier method, and comparison of survival times was performed with the log-rank test. A p value<0.05 was taken as the level of significance.

The following examples are for purposes of illustration only and are not meant to limit the invention in any way.

EXAMPLE 1

Localization of CA IX Expression in Gastric Cancer Cells

The distribution and expression pattern of CA IX was investigated by immunohistochemistry. Tissue sections were stained with anti-CA IX antibody M75. CA IX was found in the non-neoplastic gastric mucosa, intestinal metaplasia and significantly less often in gastric cancer. Occasionally the immunostaining was heterogeneous: for example, poorly differentiated (G3) intestinal type gastric cancer exhibited no immunostaining of the tumor cells in the mucosa, and intense staining in a subset of the tumor cells infiltrating the muscularis propria (Hematoxylin counterstain).

Overall, CA IX was found in non-neoplastic gastric mucosa of every patient studied. It was confined to foveolar epithelial cells, fundic and antral glands. Intestinal metaplasia was observed in 15 (26.3%) patients, and CA IX was expressed at the brush border of the intestinal metaplasia in 10 patients (66.7%). CA IX was expressed in gastric cancer cells of 31 (54.0%) patients. No differences were found between intestinal and diffuse type of gastric cancer. CA IX was present in the tumor cells of 14 (51.9%) patients with diffuse type gastric cancer, in 12 (57.1%) patients with moderately differentiated intestinal type gastric cancer and 5 (55.6%) patients with poorly differentiated intestinal type gastric cancer. The mean total immunoreactivity score for CA IX was calculated to be 1.95±1.98 for gastric cancer compared with 5.66±0.78 in the foveolar epithelium (p<0.001). Again no differences were found between diffuse or intestinal type gastric cancers. Table 1 summarizes the total immunoreactivity scores for CA IX.

TABLE 1

Expression of CA IX in gastric cancer as shown by immunohistochemistry

| Characteristics | Moderately differentiated intestinal type n = 21 | Poorly differentiated intestinal type n = 9 | Diffuse type n = 27 |
|---|---|---|---|
| Age (years ± SD) | 68.3 ± 10.0 | 60.0 ± 11.2 | 62.0 ± 11.0 |
| Gender (m/f) | 15/6 | 7/2 | 15/12 |
| [a]IRS of cancer cells | 1.67 ± 1.73 | 2.05 ± 1.99 | 1.96 ± 2.10 |
| IRS of foveolar epithelium | 5.50 ± 0.84 | 5.88 ± 0.33 | 5.52 ± 0.98 |
| [b]P-value | <0.001 | <0.001 | <0.001 |

[a]IRS denotes immunoreactivity score;
[b]The P-value refers to the differences between the IRS of cancer cells and foveolar epithelium.

EXAMPLE 2

Quantitative Analysis of CA IX Expression in Gastric Cancers

CA9 mRNA and CA IX protein expression were then assessed by realtime quantitative PCR and Western blotting. Tumor samples were obtained from 18 patients with gastric cancer and matched corresponding non-neoplastic gastric mucosa was also available from those patients. CA9 mRNA levels in cancer and non-cancer tissues were assessed in 10 patients, whereas Western blot analysis was performed in 12 cases. In 5 cases, both Western blot analysis and realtime quantitative PCR was performed in the same patient, allowing a direct comparison of the expression levels of CA IX protein and CA9 mRNA in gastric cancer and non-neoplastic gastric mucosa. Overall the levels of CA IX protein and CA9 mRNA were significantly decreased in gastric cancers compared to the matched non-neoplastic mucosa (p=0.04). The direct comparison of 5 cases in which both CA IX protein and CA9 mRNA levels were assessed, revealed that in all cases reduced protein levels were associated with decreased CA9 mRNA levels (FIG. 4).

EXAMPLE 3

Prognostic Significance of CA IX Expression in Gastric Cancer

Survival data were obtained from 23 patients with gastric cancer undergoing gastric cancer resection. According to the immunohistochemical score as outlined above two groups of patients were classified as group A with low CA IX expression (IRS≦3) versus group B with high CA IX expression in the cancer cells (IRS>3). Post-operative survival time for patients with high CA IX expression was significantly shorter than in patients without or low CA IX expression (p=0.0281) (FIG. 5). Interestingly, expression of CA IX was very prominent at the site of infiltration of the muscularis propria, indicating that despite the overall loss of CA IX expression in gastric cancer, the sustained or re-expression of CA IX at the invasion front may contribute to the overall poor survival in patients with increased CA IX expression.

EXAMPLE 4

CA IX Transfection Induces Invasion and Proliferation of AGS Cells

CA9 mRNA and CA IX protein-levels were investigated in AGS, N87 and MKN28 gastric cancer cells by realtime PCR and Western blotting. HeLa cells served as positive control. CA9 mRNA and CA IX protein were found in N87 and MKN28 cells, albeit at significantly lower levels compared to HeLa cells (FIG. 4). CA9 mRNA and CA IX protein were undetectable in AGS cells, which were then chosen for transfection of CA9 cDNA in order to assess the biological changes associated with CA IX expression. AGS cells were transfected with full-length CA9 cDNA, with an empty expression vector (control B) or were treated only with the transfectam reagent without DNA transfer (control A). The expression of CA IX in transfected cells was confirmed by Western blotting (not shown). The invasive capability of transfected AGS cells was assessed using 24-well Transwell chambers. The expression of CA IX in AGS cells resulted in a significant increase of migrating cells compared with controls, i.e. incubation of parental AGS cells with transfectam only or AGS cells transfected with empty vector (controls A and B) (FIG. 6). Furthermore, transfected AGS cells showed a significant increase in cell proliferation compared with the two control groups (FIG. 6).

EXAMPLE 5

Biological Effects of Restoration of CA IX Expression in Gastric Cancer Cells by Inhibition of Methylation The levels of CA9 mRNA were also analyzed in N87, MKN28, MKN45 and AGS cells after treatment with 5'-aza-deoxycytidine, a demethylating agent. Treatment with 5'-aza-deoxycytidine increased CA9 mRNA levels more than 5 fold in N87, MKN45 and AGS cells, indicating that the expression of CA IX is, at least in part, regulated by methylation. No effect was observed in MNK28 cells (FIG. 7). The in vitro matrigel invasion assay was used to assess the invasive potential of 5'-aza-deoxycytidine treated AGS cells compared to untreated AGS cells. Untreated AGS cells exhibited no striking difference in invasiveness as compared to DMSO treated AGS cells (control). In contrast, 2.9% of 5'-aza-deoxycytidine treated AGS cells passed the reconstituted matrigel matrix, while only 1.05% of untreated and 1.04% of DMSO treated AGS cells were detectable on the lower side of the filters ($p<0.01$) (FIG. 7).

DISCUSSION

Recent studies in renal cancer indicate that CA IX expression is, at least in part, regulated by methylation of the CA9 gene promoter and that hypomethylation of CpG at −74 bp and −6 bp sites in the CA9 promoter region is associated with increased CA IX expression in human renal cancer cell lines [32, 33]. Since as shown herein reduced or lost expression of CA IX was observed in a large number of gastric cancers and gastric cancer cell lines, 4 well-established gastric cancer cell lines were treated with 5'-aza-deoxycytidine, a demethylating agent, in order to analyze whether inhibition of methylation might lead to the restoration of CA IX expression. As described in Example 5 above, all cell lines, except for MKN28 cells, exhibited increased CA9 mRNA levels in the realtime PCR analysis after treatment with 5'-aza-deoxycytidine, indicating that the expression of CA IX in gastric cancer cell lines is, at least in part, regulated by methylation of CpG sites [see FIG. 7]. Since reexpression of CA IX was observed in those cells after treating the cells with 5'-aza-deoxycytidine, it appeared fruitful to assess, whether the restoration of CA IX expression would also alter the biological characteristics of the cells. Therefore, the cells were also analyzed in an invasion assay that allowed for the evaluation of changes in invasiveness of cells with and without treatment. While no changes were observed in the invasiveness of the AGS cells, which were kept in media or DMSO added to the media, AGS cells incubated with 5'-aza-deoxycytidine exhibited a significant, almost 3 fold increased level of invasiveness, indicating that the restoration of CA IX in those cells is associated with enhanced invasion.

Based on the data reported herein, it can be assumed that the loss of CA IX is an early event in gastric cancer, that may be associated with an increased promoter methylation. Later in the process of gastric cancer progression CA IX expression is induced at the invasion front of the cancer cells, which gives those cells an additional growth advantage by enhancing their proliferation and invasive growth. Inasmuch as HIF-1α is induced by intratumoral hypoxia, which in turn induces CA IX expression [24, 25], it is assumable that the reexpression of CA IX at the invasion front of gastric cancers may result from the activation of the $O_2$-regulated subunit of HIF-1 leading to increased HIF-1β expression at the invasion front of gastric cancers, which has already been reported in colon and other cancers [34]. In summary, while the frequent loss of CA IX expression observed in gastric cancer may be an early event, the overexpression of CA IX at the invasion front of a subset of gastric cancers may lead to invasive growth and thereby contributes to the growth and progression of gastric cancer malignancy. The inventors then conclude that preneoplastic/neoplastic diseases having similar CA IX expression patterns as that of gastric cancer would also be subject to the prognostic methods disclosed herein.

BUDAPEST TREATY DEPOSITS

The materials listed below were deposited with the American Type Culture Collection (ATCC) now at 10810 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

|  | Deposit Date | ATCC # |
|---|---|---|
| Hybridoma | | |
| VU-M75 | Sep. 17, 1992 | HB 11128 |
| MN 12.2.2 | Jun. 9, 1994 | HB 11647 |
| Plasmid | | |
| A4a | Jun. 6, 1995 | 97199 |
| XE1 | Jun. 6, 1995 | 97200 |
| XE3 | Jun. 6, 1995 | 97198 |

Similarly, the hybridoma cell line V/10-VU which produces the V/10 monoclonal antibodies was deposited on Feb. 19, 2003 under the Budapest Treaty at the International Depository Authority (IDA) of the Belgian Coordinated Collections of Microorganisms (BCCM) at the Laboratorium voor Moleculaire Biologie-Plasmidencollectie (LMBP) at the Universeit Gent, K. L. Ledeganckstraat 35, B-9000 Gent, Belgium [BCCM/LMBP] under the Accession No. LMBP 6009CB.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method which is prognostic for a gastric preneoplastic/neoplastic disease afflicting a subject vertebrate, said method comprising:
    (a) detecting MN/CA IX protein or MN/CA IX polypeptide in a gastric preneoplastic/neoplastic tissue sample comprising neoplastic cells taken from said vertebrate,
    (b) quantitating the level of said MN/CA IX protein or MN/CA IX polypeptide in said sample,
    (c) comparing the level of MN/CA IX protein or MN/CA IX polypeptide of step (b) to the average level of MN/CA IX protein or MN/CA IX polypeptide in comparable gastric preneoplastic/neoplastic tissue samples comprising neoplastic cells taken from vertebrates also afflicted by a gastric preneoplastic/neoplastic disease, wherein said vertebrates are of the same species as the subject vertebrate, and
    (d) determining that said subject vertebrate has a prognosis of shorter survival if the level of MN/CA IX protein or MN/CA IX polypeptide of step (b) is higher than the average level of MN/CA IX protein or MN/CA IX polypeptide in said comparable gastric preneoplastic/neoplastic tissue samples, than if said MN/CA IX protein or MN/CA IX polypeptide of step (b) were absent or at a significantly reduced level in said sample relative to said average level;
    wherein said MN/CA IX protein is encoded by a nucleotide sequence selected from the group consisting of:
    (1) SEQ ID NO: 1's coding region;
    (2) nucleotide sequences that hybridize under stringent hybridization conditions of 50% formamide at 42 degree C. to complement of SEQ ID NO: 1's coding region; and
    (3) nucleotide sequences that differ from SEQ ID NO: 1's coding region or from the nucleotide sequences of (2) in codon sequence due to the degeneracy of the genetic code;
    wherein said MN/CA IX protein or said MN/CA IX polypeptide is specifically bound by the M75 monoclonal antibody that is secreted from the hybridoma VU-M75, which was deposited at the American Type Culture Collection under ATCC No. HB 11128.

2. The method of claim 1 wherein said disease is gastric cancer, and wherein said sample is taken from the invasion front of said gastric cancer.

3. The method of claim 1 wherein said disease is a gastric tumor, and said sample is taken from said gastric tumor and/or from a metastatic lesion derived from said gastric tumor.

4. The method of claim 1, wherein immunohistochemical staining with MN/CA IX-specific antibody is used to detect and quantitate MN/CA IX protein in the sample, and wherein the quantitating step (b) comprises determining an immunoreactivity score of cells in said sample comprising:
- (b1) determining the percentage of immunoreactive cells, wherein the percentage of immunoreactive cells is assigned
  - a value of 0 if no immunoreactive cells,
  - a value of 1 if less than 10% immunoreactive cells,
  - a value of 2 if between 11% and 50% immunoreactive cells, or
  - a value of 3 if more than 50% immunoreactive cells;
- (b2) determining the intensity of immunostaining of the immunoreactive cells, wherein the intensity of MN/CA IX immunostaining is assigned
  - a value of 0 for staining equal to a negative control,
  - a value of 1 for weak staining,
  - a value of 2 for moderate staining, or
  - a value of 3 for strong staining; and
- (b3) adding the value for the percentage of immunoreactive cells found in step (b1) and the value for the intensity of immunostaining found in step (b2) to obtain the immunoreactivity score;
- wherein the comparing step (c) comprises determining the immunoreactivity scores of said comparable samples analogously to the determination of the immunoreactivity score of the sample from the subject vertebrate in steps b(1) to b(3), and averaging said immunoreactivity scores from said comparable samples; and
- wherein if the immunoreactivity score of the subject vertebrate sample determined in steps b(1) to b(3) is above the average immunoreactivity score of said comparable samples, concluding in step (d) that said vertebrate has a prognosis of shorter survival than if said immunoreactivity score is at or below said average immunoreactivity score.

5. The method of claim 1, wherein said disease comprises a gastric tumor, or a gastric tumor and one or more metastatic lesions derived from the gastric tumor, and wherein prognosis is measured in terms of shortened survival following treatment and/or surgical removal of the tumor, or the tumor and said one or more metastatic lesions.

6. The method of claim 1, wherein said gastric preneoplastic/neoplastic tissue sample is a formalin-fixed, paraffin-embedded tissue sample or a frozen tissue sample.

7. The method according to claim 1, wherein said detecting step (a) comprises the use of an assay selected from the group consisting of Western blots, enzyme-inked immunosorbent assays, radioimmunoassays, competition immunoassays, dual antibody sandwich assays, immunohistochemical staining assays, agglutination assays, fluorescent immunoassays cytofluorometry.

8. The method according to claim 1, wherein said detecting step (a) comprises the use of the monoclonal antibody secreted by the hybridoma VU-M75 which has Accession No. ATCC HB 11128.

9. The method according to claim 1, wherein the detecting step (a) is by immunohistochemical staining, and wherein the quantitating step (b) comprises determining the percentage and/or the intensity of immunostaining of immunoreactive cells.

10. The method of claim 1, wherein said vertebrate is a mammal.

11. The method of claim 10, wherein said mammal is a human.

12. The method of claim 1, wherein said prognostic method is used as an aid in the selection of treatment for said gastric preneoplastic/neoplastic disease afflicting said vertebrate, further comprising concluding that said patient is a high risk patient in need of adjuvant therapies, if said determination in step (d) indicates a prognosis of shortened survival.

13. The method of claim 1 wherein said sample is taken from the invasion front of said gastric preneoplastic/neoplastic disease, and said comparable samples are analogous invasion front samples.

14. The method of claim 13 wherein said preneoplastic/neoplastic disease is a neoplastic disease.

15. A method which is prognostic for a gastric preneoplastic/neoplastic disease afflicting a subject vertebrate, wherein said disease is present in a gastric tissue in which 40% or more of the cells normally express MN/CA IX protein, but said gastric tissue loses MN/CA IX expression or expression of MN/CA IX is significantly reduced upon carcinogenesis, said method comprising:
- (a) taking a gastric tissue sample comprising neoplastic cells from the invasion front of said preneoplastic/neoplastic disease;
- (b) determining whether MN/CA IX protein or MN/CA IX polypeptide is absent or at a significantly reduced level in said gastric invasion front sample as compared to the level that said MN/CA IX protein or MN/CA IX polypeptide is normally expressed in said gastric tissue, when said gastric tissue is unaffected by said disease; and
- (c) concluding that if said MN/CA IX protein or MN/CA IX polypeptide is neither absent nor at such a significantly reduced level in said invasion front sample, that the subject vertebrate has a prognosis of shorter survival than if said MN/CA IX protein or MN/CA IX polypeptide were absent or at a such a significantly reduced level in said invasion front sample.

* * * * *

UNITED STATES PATENT AND TRADEMARK OFFICE
CERTIFICATE OF CORRECTION

PATENT NO.        : 7,524,634 B2
APPLICATION NO.   : 10/575300
DATED             : April 28, 2009
INVENTOR(S)       : Matthias Ebert et al.

Page 1 of 1

It is certified that error appears in the above-identified patent and that said Letters Patent is hereby corrected as shown below:

Cover Page, item (74),
"Lieona L. Lauder" should read -- Leona L. Lauder --.

Signed and Sealed this

Ninth Day of June, 2009

JOHN DOLL
*Acting Director of the United States Patent and Trademark Office*

SEQUENCE LISTING

<160> NUMBER OF SEQ ID NOS: 11

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1

```
acagtcagcc gc atg gct ccc ctg tgc ccc agc ccc tgg ctc cct ctg ttg       51
           Met Ala Pro Leu Cys Pro Ser Pro Trp Leu Pro Leu Leu
               -35             -30                 -25 atc ccg gcc cct gct cca ggc ctc act gtg caa ctg ctg tca ctg              99
Ile Pro Ala Pro Ala Pro Gly Leu Thr Val Gln Leu Leu Ser Leu
            -20                 -15                 -10 ctg ctt ctg atg cct gtc cat ccc cag agg ttg ccc cgg atg cag gag         147
Leu Leu Leu Met Pro Val His Pro Gln Arg Leu Pro Arg Met Gln Glu
        -5                  -1  1                   5 gat tcc ccc ttg gga gga ggc tct tct ggg gaa gat gac cca ctg ggc         195
Asp Ser Pro Leu Gly Gly Gly Ser Ser Gly Glu Asp Asp Pro Leu Gly
    10                  15                  20 gag gag gat ctg ccc agt gaa gag gat tca ccc aga gag gag gat cca         243
Glu Glu Asp Leu Pro Ser Glu Glu Asp Ser Pro Arg Glu Glu Asp Pro
25                  30                  35                  40 ccc gga gag gag gat cta cct gga gag gag gat cta cct gga gag gag         291
Pro Gly Glu Glu Asp Leu Pro Gly Glu Glu Asp Leu Pro Gly Glu Glu
                45                  50                  55 gat cta cct gaa gtt aag cct aaa tca gaa gaa gag ggc tcc ctg aag         339
Asp Leu Pro Glu Val Lys Pro Lys Ser Glu Glu Glu Gly Ser Leu Lys
            60                  65                  70 tta gag gat cta cct act gtt gag gct cct gga gat cct caa gaa ccc         387
Leu Glu Asp Leu Pro Thr Val Glu Ala Pro Gly Asp Pro Gln Glu Pro
        75                  80                  85 cag aat aat gcc cac agg gac aaa gaa ggg gat gac cag agt cat tgg         435
Gln Asn Asn Ala His Arg Asp Lys Glu Gly Asp Asp Gln Ser His Trp
    90                  95                  100 cgc tat gga ggc gac ccg ccc tgg ccc cgg gtg tcc cca gcc tgc gcg         483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc         531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg         579
Cys Pro Ala Leu Arg Pro Leu Glu Leu Leu Gly Phe Gln Leu Pro Pro
            140                 145                 150 ctc cca gaa ctg cgc ctg cgc aac aat ggc cac agt gtg caa ctg acc         627
Leu Pro Glu Leu Arg Leu Arg Asn Asn Gly His Ser Val Gln Leu Thr
        155                 160                 165 ctg cct cct ggg cta gag atg gct ctg ggt ccc ggg cgg gag tac cgg         675
Leu Pro Pro Gly Leu Glu Met Ala Leu Gly Pro Gly Arg Glu Tyr Arg
    170                 175                 180 gct ctg cag ctg cat ctg cac tgg ggg gct gca ggt cgt ccg ggc tcg         723
Ala Leu Gln Leu His Leu His Trp Gly Ala Ala Gly Arg Pro Gly Ser
185                 190                 195                 200 gag cac act gtg gaa ggc cac cgt ttc cct gcc gag atc cac gtg gtt         771
```

```
                                                                              -continued Glu His Thr Val Glu Gly His Arg Phe Pro Ala Glu Ile His Val Val
            205                 210                 215 cac ctc agc acc gcc ttt gcc aga gtt gac gag gcc ttg ggg cgc ccg        819
His Leu Ser Thr Ala Phe Ala Arg Val Asp Glu Ala Leu Gly Arg Pro
            220                 225                 230 gga ggc ctg gcc gtg ttg gcc gcc ttt ctg gag gag ggc ccg gaa gaa        867
Gly Gly Leu Ala Val Leu Ala Ala Phe Leu Glu Glu Gly Pro Glu Glu
            235                 240                 245 aac agt gcc tat gag cag ttg ctg tct cgc ttg gaa gaa atc gct gag        915
Asn Ser Ala Tyr Glu Gln Leu Leu Ser Arg Leu Glu Glu Ile Ala Glu
        250                 255                 260 gaa ggc tca gag act cag gtc cca gga ctg gac ata tct gca ctc ctg        963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca       1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg       1059
Pro Pro Cys Ala Gln Gly Val Ile Trp Thr Val Phe Asn Gln Thr Val
            300                 305                 310 atg ctg agt gct aag cag ctc cac acc ctc tct gac acc ctg tgg gga       1107
Met Leu Ser Ala Lys Gln Leu His Thr Leu Ser Asp Thr Leu Trp Gly
            315                 320                 325 cct ggt gac tct cgg cta cag ctg aac ttc cga gcg acg cag cct ttg       1155
Pro Gly Asp Ser Arg Leu Gln Leu Asn Phe Arg Ala Thr Gln Pro Leu
            330                 335                 340 aat ggg cga gtg att gag gcc tcc ttc cct gct gga gtg gac agc agt       1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt       1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc       1299
Asp Ile Leu Ala Leu Val Phe Gly Leu Leu Phe Ala Val Thr Ser Val
            380                 385                 390 gcg ttc ctt gtg cag atg aga agg cag cac aga agg gga acc aaa ggg       1347
Ala Phe Leu Val Gln Met Arg Arg Gln His Arg Arg Gly Thr Lys Gly
            395                 400                 405 ggt gtg agc tac cgc cca gca gag gta gcc gag act gga gcc                1389
Gly Val Ser Tyr Arg Pro Ala Glu Val Ala Glu Thr Gly Ala
            410                 415                 420 tagaggctgg atcttggaga atgtgagaag ccagccagag gcatctgagg gggagccggt     1449
aactgtcctg tcctgctcat tatgccactt ccttttaact gccaagaaat tttttaaaat     1509
aaatatttat aat                                                        1522

<210> SEQ ID NO 2
<211> LENGTH: 459
<212> TYPE: PRT
<213> ORGANISM: Homo sapiens

<400> SEQUENCE: 2

Met Ala Pro Leu Cys Pro Ser Pro Trp Leu Pro Leu Leu Ile Pro Ala
            -35                 -30                 -25

Pro Ala Pro Gly Leu Thr Val Gln Leu Leu Leu Ser Leu Leu Leu Leu
        -20                 -15                 -10

Met Pro Val His Pro Gln Arg Leu Pro Arg Met Gln Glu Asp Ser Pro
-5                  -1   1               5                  10

Leu Gly Gly Gly Ser Ser Gly Glu Asp Asp Pro Leu Gly Glu Glu Asp
```

```
                  15                  20                  25
Leu Pro Ser Glu Glu Asp Ser Arg Glu Asp Pro Gly Glu
        30                  35                  40
Glu Asp Leu Pro Gly Glu Asp Leu Pro Gly Glu Asp Leu Pro
        45                  50                  55
Glu Val Lys Pro Lys Ser Glu Glu Gly Ser Leu Lys Leu Glu Asp
60                  65                  70                  75
Leu Pro Thr Val Glu Ala Pro Gly Asp Pro Gln Glu Pro Gln Asn Asn
                80                  85                  90
Ala His Arg Asp Lys Glu Gly Asp Gln Ser His Trp Arg Tyr Gly
            95                  100                 105
Gly Asp Pro Pro Trp Pro Arg Val Ser Pro Ala Cys Ala Gly Arg Phe
        110                 115                 120
Gln Ser Pro Val Asp Ile Arg Pro Gln Leu Ala Ala Phe Cys Pro Ala
        125                 130                 135
Leu Arg Pro Leu Glu Leu Leu Gly Phe Gln Leu Pro Pro Leu Pro Glu
140                 145                 150                 155
Leu Arg Leu Arg Asn Asn Gly His Ser Val Gln Leu Thr Leu Pro Pro
                160                 165                 170
Gly Leu Glu Met Ala Leu Gly Pro Gly Arg Glu Tyr Arg Ala Leu Gln
            175                 180                 185
Leu His Leu His Trp Gly Ala Ala Gly Arg Pro Gly Ser Glu His Thr
        190                 195                 200
Val Glu Gly His Arg Phe Pro Ala Glu Ile His Val Val His Leu Ser
        205                 210                 215
Thr Ala Phe Ala Arg Val Asp Glu Ala Leu Gly Arg Pro Gly Gly Leu
220                 225                 230                 235
Ala Val Leu Ala Ala Phe Leu Glu Glu Gly Pro Glu Glu Asn Ser Ala
                240                 245                 250
Tyr Glu Gln Leu Leu Ser Arg Leu Glu Glu Ile Ala Glu Glu Gly Ser
            255                 260                 265
Glu Thr Gln Val Pro Gly Leu Asp Ile Ser Ala Leu Leu Pro Ser Asp
        270                 275                 280
Phe Ser Arg Tyr Phe Gln Tyr Glu Gly Ser Leu Thr Thr Pro Pro Cys
        285                 290                 295
Ala Gln Gly Val Ile Trp Thr Val Phe Asn Gln Thr Val Met Leu Ser
300                 305                 310                 315
Ala Lys Gln Leu His Thr Leu Ser Asp Thr Leu Trp Gly Pro Gly Asp
                320                 325                 330
Ser Arg Leu Gln Leu Asn Phe Arg Ala Thr Gln Pro Leu Asn Gly Arg
            335                 340                 345
Val Ile Glu Ala Ser Phe Pro Ala Gly Val Asp Ser Ser Pro Arg Ala
        350                 355                 360
Ala Glu Pro Val Gln Leu Asn Ser Cys Leu Ala Ala Gly Asp Ile Leu
        365                 370                 375
Ala Leu Val Phe Gly Leu Leu Phe Ala Val Thr Ser Val Ala Phe Leu
380                 385                 390                 395
Val Gln Met Arg Arg Gln His Arg Arg Gly Thr Lys Gly Gly Val Ser
                400                 405                 410
Tyr Arg Pro Ala Glu Val Ala Glu Thr Gly Ala
            415                 420

<210> SEQ ID NO 3
```

<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3

```
ggatcctgtt gactcgtgac cttaccccca accctgtgct ctctgaaaca tgagctgtgt      60
ccactcaggg ttaaatggat taagggcggt gcaagatgtg ctttgttaaa cagatgcttg     120
aaggcagcat gctcgttaag agtcatcacc aatccctaat ctcaagtaat cagggacaca     180
aacactgcgg aaggccgcag ggtcctctgc ctaggaaaac cagagacctt tgttcacttg     240
tttatctgac cttccctcca ctattgtcca tgaccctgcc aaatcccct ctgtgagaaa      300 cacccaagaa ttatcaataa aaaataaat ttaaaaaaaa aatacaaaaa aaaaaaaaa       360 aaaaaaaaaa gacttacgaa tagttattga taaatgaata gctattggta aagccaagta     420
aatgatcata ttcaaaacca gacggccatc atcacagctc aagtctacct gatttgatct     480
ctttatcatt gtcattcttt ggattcacta gattagtcat catcctcaaa attctccccc     540
aagttctaat tacgttccaa acatttaggg gttacatgaa gcttgaacct actaccttct     600
ttgcttttga gccatgagtt gtaggaatga tgagtttaca ccttacatgc tggggattaa     660
tttaaacttt acctctaagt cagttgggta gcctttggct tattttgta gctaattttg      720 tagttaatgg atgcactgtg aatcttgcta tgatagtttt cctccacact ttgccactag     780
gggtaggtag gtactcagtt ttcagtaatt gcttacctaa gaccctaagc cctatttctc     840
ttgtactggc ctttatctgt aatatgggca tatttaatac aatataattt ttggagtttt     900
tttgtttgtt tgtttgtttg ttttttgag acggagtctt gcatctgtca tgcccaggct     960
ggagtagcag tggtgccatc tcggctcact gcaagctcca cctcccgagt tcacgccatt    1020
ttcctgcctc agcctcccga gtagctggga ctacaggcgc cgccaccat gcccggctaa     1080 ttttttgtat ttttggtaga acggggtttt caccgtgtta gccagaatgg tctcgatctc    1140
ctgacttcgt gatccacccg cctcggcctc ccaaagttct gggattacag gtgtgagcca    1200
ccgcacctgg ccaattttt gagtctttta aagtaaaaat atgtcttgta agctggtaac     1260
tatggtacat ttccttttat taatgtggtg ctgacggtca tataggttct tttgagtttg    1320
gcatgcatat gctactttt gcagtccttt cattacattt ttctctcttc atttgaagag     1380
catgttatat cttttagctt cacttggctt aaaaggttct ctcattagcc taacacagtg    1440
tcattgttgg taccacttgg atcataagtg gaaaaacagt caagaaattg cacagtaata    1500
cttgtttgta agagggatga ttcaggtgaa tctgacacta agaaactccc ctacctgagg    1560
tctgagattc ctctgacatt gctgtatata ggcttttcct ttgacagcct gtgactgcgg    1620 actattttc ttaagcaaga tatgctaaag tttttgtgagc ctttttccag agagaggtct     1680
catatctgca tcaagtgaga acatataatg tctgcatgtt tccatatttc aggaatgttt    1740
gcttgtgttt tatgctttta tatagacagg gaaacttgtt cctcagtgac ccaaaagagg    1800
tgggaattgt tattggatat catcattggc ccacgctttc tgaccttgga aacaattaag    1860
ggttcataat ctcaattctg tcagaattgg tacaagaaat agctgctatg tttcttgaca    1920
ttccacttgg taggaaataa gaatgtgaaa ctcttcagtt ggtgtgtgtc cctngttttt    1980
```

```
ttgcaatttc cttcttactg tgttaaaaaa aagtatgatc ttgctctgag aggtgaggca    2040
ttcttaatca tgatctttaa agatcaataa tataatcctt tcaaggatta tgtctttatt    2100
ataataaaga taatttgtct ttaacagaat caataatata atcccttaaa ggattatatc    2160
tttgctgggc gcagtggctc acacctgtaa tcccagcact ttgggtggcc aaggtggaag    2220
gatcaaattt gcctacttct atattatctt ctaaagcaga attcatctct cttccctcaa    2280
tatgatgata ttgacagggt ttgccctcac tcactagatt gtgagctcct gctcagggca    2340
ggtagcgttt tttgttttttg ttttttgtttt tctttttttga cagggtct tgctctgtca    2400 cccaggccag agtgcaatgg tacagtctca gctcactgca gcctcaaccg cctcggctca    2460
aaccatcatc ccatttcagc ctcctgagta gctgggacta caggcacatg ccattacacc    2520
tggctaattt ttttgtattt ctagtagaga cagggtttgg ccatgttgcc cgggctggtc    2580
tcgaactcct ggactcaagc aatccaccca cctcagcctc caaaatgag gaccgtgtc    2640 ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060 ggctcccta gcagcctgcc ctacctcttt acctgcttcc tggtggagtc agggatgtat    3120
acatgagctg ctttccctct cagccagagg acatggggggg ccccagctcc cctgcctttc    3180
cccttctgtg cctggagctg ggaagcaggc cagggttagc tgaggctggc tggcaagcag    3240
ctgggtggtg ccagggagag cctgcatagt gccaggtggt gccttgggtt ccaagctagt    3300
ccatggcccc gataaccttc tgcctgtgca cacacctgcc cctcactcca ccccatcct    3360 agctttggta tggggagag ggcacagggc cagacaaacc tgtgagactt tggctccatc    3420
tctgcaaaag ggcgctctgt gagtcagcct gctcccctcc aggcttgctc ctcccccacc    3480
cagctctcgt ttccaatgca cgtacagccc gtacacaccg tgtgctggga cacccccacag   3540 tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200 tggagaagag aaagggatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
```

```
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt tttttttttt ttttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagcaatga    4920 ttgcaagctg gtaggattgc tgtttggccc acccagctgc ggtgttgagt ttgggtgcgg    4980
tctcctgtgc tttgcacctg cccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacagggat gaccagagtc attggcgcta tggaggtgag    5160
acacccaccc gctgcacaga cccaatctgg gaacccagct ctgtggatct cccctacagc    5220
cgtccctgaa cactggtccc gggcgtccca ccgccgccc accgtcccac cccctcacct    5280
tttctacccg ggttccctaa gttcctgacc taggcgtcag acttcctcac tatactctcc    5340 cacccccaggc gacccgccct ggccccgggt gtccccagcc tgcgcgggcc gcttccagtc    5400
cccggtggat atccgccccc agctcgccgc cttctgcccg gccctgcgcc ccctggaact    5460
cctgggcttc cagctcccgc cgctcccaga actgcgcctg cgcaacaatg gccacagtgg    5520 tgaggggtc tccccgccga acttggggga tggggcgggg cgcaggaaag gaaccgtcg    5580 cgcagtgcct gcccgggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tgggggctg caggtcgtcc gggctcggag    5760
cacactgtgg aaggccaccg tttccctgcc gaggtgagcg cggactggcc gagaaggggc    5820
aaaggagcgg ggcggacggg ggccagagac gtggccctct cctaccctcg tgtccttttc    5880
agatccacgt ggttcacctc agcaccgcct ttgccagagt tgacgaggcc ttggggcgcc    5940
cgggaggcct ggccgtgttg gccgccttc tggaggtacc agatcctgga cacccctac    6000 tccccgcttt cccatcccat gctcctcccg gactctatcg tggagccaga gccccatcc    6060 cagcaagctc actcaggccc ctggctgaca aactcattca cgcactgttt gttcatttaa    6120
cacccactgt gaaccaggca ccagccccca acaaggattc tgaagctgta ggtccttgcc    6180
tctaaggagc ccacagccag tgggggaggc tgacatgaca gacacatagg aaggacatag    6240
taaagatggt ggtcacagag gaggtgacac ttaaagcctt cactggtaga aaagaaaagg    6300
aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt tttttgtatt tttagtagac agggtttcac catgttggtc aggctggtct    6660
caaactcctg gcctcaagtg atccgcctga ctcagcctac caaagtgctg attacaagtg    6720
```

```
tgagccaccg tgcccagcca cactcactga ttctttaatg ccagccacac agcacaaagt    6780
tcagagaaat gcctccatca tagcatgtca atatgttcat actcttaggt tcatgatgtt    6840
cttaacatta ggttcataag caaaataaga aaaagaata ataaataaaa gaagtggcat      6900
gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaaccagtcc accaagcttg ttggttcgca    7140
cagcaagagt acatagagtt tgaaataata cataggattt taagagggag acactgtctc    7200
taaaaaaaaa aacaacagca acaacaaaaa gcaacaacca ttacaatttt atgttccctc    7260
agcattctca gagctgagga atgggagagg actatgggaa ccccttcat gttccggcct     7320 tcagccatgg ccctggatac atgcactcat ctgtcttaca atgtcattcc cccaggaggg    7380 cccgaagaa aacagtgcct atgagcagtt gctgtctcgc ttggaagaaa tcgctgagga     7440
aggtcagttt gttggtctgg ccactaatct ctgtggccta gttcataaag aatcacccct     7500
tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt gggaggccaa ggcaggtgga tcacgaggtc aagagatcaa gaccatcctg    7740
gccaacatgt gaaacccca tctctactaa aaatacgaaa aaatagccag gcgtggtggc     7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaa aaaaaaaaa gaaaaccaag caaaaccaa atgagacaa         7980 aaaaacaag accaaaaaat ggtgtttgga aattgtcaag gtcaagtctg gagagctaaa     8040 cttttctga gaactgttta tctttaataa gcatcaaata ttttaacttt gtaaatactt     8100
ttgttggaaa tcgttctctt cttagtcact cttgggtcat tttaaatctc acttactcta    8160
ctagaccttt taggtttctg ctagactagg tagaactctg cctttgcatt tcttgtgtct    8220
gttttgtata gttatcaata ttcatattta tttacaagtt attcagatca ttttttcttt    8280 tcttttttt ttttttttt tttttacat ctttagtaga gacagggttt caccatattg        8340
gccaggctgc tctcaaactc ctgaccttgt gatccaccag cctcggcctc ccaaagtgct    8400
gggattcatt tttctttt aatttgctct gggcttaaac ttgtggccca gcactttatg       8460
atggtacaca gagttaagag tgtagactca gacggtcttt cttctttcct tctcttcctt    8520
cctcccttcc ctcccacctt cccttctctc cttcctttct ttcttcctct cttgcttcct    8580
caggcctctt ccagttgctc caaagccctg tactttttt tgagttaacg tcttatggga     8640
agggcctgca cttagtgaag aagtggtctc agagttgagt taccttggct tctgggaggt    8700
gaaactgtat ccctataccc tgaagcttta aggggtgca atgtagatga daccccaaca    8760
tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaagagg atgtaagatg agatgagaaa     9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
```

-continued

```
agtgtgaccc catctctacc aaaaaaaccc caacaaaacc aaaaatagcc gggcatggtg    9180
gtatgcggcc tagtcccagc tactcaagga ggctgaggtg ggaagatcgc ttgattccag    9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg accttgtttc ctgtcatgc catgaaccca     9420
cccacactgt ccactgacct ccctagctcc acaccctctc tgacaccctg tggggacctg    9480
gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
tgtctggttt cccccagcc agtagtccct tatcctccca tgtgtgtgcc agtgtctgtc     9660
attggtggtc acagcccgcc tctcacatct ccttttctc tccagtccag ctgaattcct     9720
gcctggctgc tggtgagtct gcccctcctc ttggtcctga tgccaggaga ctcctcagca    9780
ccattcagcc ccagggctgc tcaggaccgc ctctgctccc tctcctttc tgcagaacag     9840
accccaaccc caatattaga gaggcagatc atggtgggga ttcccccatt gtccccagag    9900
gctaattgat tagaatgaag cttgagaaat ctcccagcat ccctctcgca aaagaatccc    9960
ccccccttt tttaaagata gggtctcact ctgtttgccc caggctgggg tgttgtggca    10020
cgatcatagc tcactgcagc ctcgaactcc taggctcagg caatcctttc accttagctt   10080
ctcaaagcac tgggactgta ggcatgagcc actgtgcctg gccccaaacg gccctttac    10140
ttggctttta ggaagcaaaa acggtgctta tcttacccct tctcgtgtat ccaccctcat   10200
cccttggctg gcctcttctg gagactgagg cactatgggg ctgcctgaga actcggggca   10260
ggggtggtgg agtgcactga ggcaggtgtt gaggaactct gcagacccct cttccttccc   10320
aaagcagccc tctctgctct ccatcgcagg tgacatccta gccctggttt ttggcctcct   10380
ttttgctgtc accagcgtcg cgttccttgt gcagatgaga aggcagcaca ggtattacac   10440
tgaccctttc ttcaggcaca agcttccccc acccttgtgg agtcacttca tgcaaagcgc   10500
atgcaaatga gctgctcctg ggccagtttt ctgattagcc tttcctgttg tgtacacaca   10560
gaaggggaac caaagggggt gtgagctacc gcccagcaga ggtagccgag actggagcct   10620
agaggctgga tcttggagaa tgtgagaagc cagccagagg catctgaggg ggagccggta   10680
actgtcctgt cctgctcatt atgccacttc cttttaactg ccaagaaatt ttttaaaata   10740
aatatttata ataaaatatg tgttagtcac ctttgttccc caaatcagaa ggaggtattt   10800
gaatttccta ttactgttat tagcaccaat ttagtggtaa tgcatttatt ctattacagt   10860
tcggcctcct tccacacatc actccaatgt gttgctcc                           10898
```

<210> SEQ ID NO 4
<211> LENGTH: 59
<212> TYPE: PRT
<213> ORGANISM: Homo sapiens

<400> SEQUENCE: 4

```
Ser Ser Gly Glu Asp Asp Pro Leu Gly Glu Asp Leu Pro Ser Glu
 1               5                  10                  15

Glu Asp Ser Pro Arg Glu Glu Asp Pro Pro Gly Glu Glu Asp Leu Pro
            20                  25                  30

Gly Glu Glu Asp Leu Pro Gly Glu Glu Asp Leu Pro Glu Val Lys Pro
        35                  40                  45

Lys Ser Glu Glu Glu Gly Ser Leu Lys Leu Glu
```

```
                    50                  55

<210> SEQ ID NO 5
<211> LENGTH: 257
<212> TYPE: PRT
<213> ORGANISM: Homo sapiens

<400> SEQUENCE: 5

Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30

Arg Pro Gln Leu Ala Ala Phe Cys Pro Ala Leu Arg Pro Leu Glu Leu
        35                  40                  45

Leu Gly Phe Gln Leu Pro Pro Leu Pro Glu Leu Arg Leu Arg Asn Asn
    50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
        115                 120                 125

Asp Glu Ala Leu Gly Arg Pro Gly Gly Leu Ala Val Leu Ala Ala Phe
    130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
            180                 185                 190

Tyr Glu Gly Ser Leu Thr Thr Pro Pro Cys Ala Gln Gly Val Ile Trp
        195                 200                 205

Thr Val Phe Asn Gln Thr Val Met Leu Ser Ala Lys Gln Leu His Thr
    210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro

<210> SEQ ID NO 6
<211> LENGTH: 37
<212> TYPE: PRT
<213> ORGANISM: Homo sapiens

<400> SEQUENCE: 6

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Met Pro Val His Pro
        35

<210> SEQ ID NO 7
```

```
<211> LENGTH: 377
<212> TYPE: PRT
<213> ORGANISM: Homo sapiens

<400> SEQUENCE: 7

Gln Arg Leu Pro Arg Met Gln Glu Asp Ser Pro Leu Gly Gly Ser
1               5                   10                  15

Ser Gly Glu Asp Asp Pro Leu Gly Glu Glu Asp Leu Pro Ser Glu Glu
                20                  25                  30

Asp Ser Pro Arg Glu Glu Asp Pro Gly Glu Glu Asp Leu Pro Gly
                35                  40                  45

Glu Glu Asp Leu Pro Gly Glu Glu Asp Leu Pro Glu Val Lys Pro Lys
50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Asp Pro Pro Trp
                100                 105                 110

Pro Arg Val Ser Pro Ala Cys Ala Gly Arg Phe Gln Ser Pro Val Asp
                115                 120                 125

Ile Arg Pro Gln Leu Ala Ala Phe Cys Pro Ala Leu Arg Pro Leu Glu
130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Gly Leu Glu Met Ala
                165                 170                 175

Leu Gly Pro Gly Arg Glu Tyr Arg Ala Leu Gln Leu His Leu His Trp
                180                 185                 190

Gly Ala Ala Gly Arg Pro Gly Ser Glu His Thr Val Glu Gly His Arg
                195                 200                 205

Phe Pro Ala Glu Ile His Val Val His Leu Ser Thr Ala Phe Ala Arg
210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
                260                 265                 270

Gly Leu Asp Ile Ser Ala Leu Leu Pro Ser Asp Phe Ser Arg Tyr Phe
                275                 280                 285

Gln Tyr Glu Gly Ser Leu Thr Thr Pro Pro Cys Ala Gln Gly Val Ile
290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
                340                 345                 350

Phe Pro Ala Gly Val Asp Ser Ser Pro Arg Ala Ala Glu Pro Val Gln
                355                 360                 365

Leu Asn Ser Cys Leu Ala Ala Gly Asp
                370                 375
```

```
<210> SEQ ID NO 8
<211> LENGTH: 20
<212> TYPE: PRT
<213> ORGANISM: Homo sapiens

<400> SEQUENCE: 8

Ile Leu Ala Leu Val Phe Gly Leu Leu Phe Ala Val Thr Ser Val Ala
1               5                   10                  15

Phe Leu Val Gln
            20

<210> SEQ ID NO 9
<211> LENGTH: 25
<212> TYPE: PRT
<213> ORGANISM: Homo sapiens

<400> SEQUENCE: 9

Met Arg Arg Gln His Arg Arg Gly Thr Lys Gly Gly Val Ser Tyr Arg
1               5                   10                  15

Pro Ala Glu Val Ala Glu Thr Gly Ala
            20                  25

<210> SEQ ID NO 10
<211> LENGTH: 19
<212> TYPE: DNA
<213> ORGANISM: Homo sapiens

<400> SEQUENCE: 10
aggaggatct gcccagtga                                          19

<210> SEQ ID NO 11
<211> LENGTH: 19
<212> TYPE: DNA
<213> ORGANISM: Homo sapiens

<400> SEQUENCE: 11
gccaatgact ctggtcatc                                          19
```